United States Patent
Fangrow

(10) Patent No.: US 10,420,927 B2
(45) Date of Patent: Sep. 24, 2019

(54) SYSTEMS, METHODS, AND COMPONENTS FOR TRANSFERRING MEDICAL FLUIDS

(71) Applicant: ICU Medical, Inc., San Clemente, CA (US)

(72) Inventor: Thomas F. Fangrow, Mission Viejo, CA (US)

(73) Assignee: ICU Medical, Inc., San Clemente, CA (US)

(*) Notice: Subject to any disclaimer, the term of this patent is extended or adjusted under 35 U.S.C. 154(b) by 0 days.

(21) Appl. No.: 16/182,503

(22) Filed: Nov. 6, 2018

(65) Prior Publication Data

US 2019/0070405 A1 Mar. 7, 2019

Related U.S. Application Data

(60) Division of application No. 15/991,385, filed on May 29, 2018, now Pat. No. 10,188,849, which is a
(Continued)

(51) Int. Cl.
*A61M 39/22* (2006.01)
*A61J 3/00* (2006.01)
(Continued)

(52) U.S. Cl.
CPC .......... *A61M 39/223* (2013.01); *A61J 1/1475* (2013.01); *A61J 1/2068* (2015.05);
(Continued)

(58) Field of Classification Search
CPC .... A61M 39/223; A61M 39/24; A61M 5/142; A61M 2039/242; A61M 2005/14506;
(Continued)

(56) References Cited

U.S. PATENT DOCUMENTS 1,923,501 A 8/1933 Perry
3,157,201 A * 11/1964 Littmann ............ A61M 39/223
137/625.47
(Continued)

FOREIGN PATENT DOCUMENTS

CN 1707379 12/2005
CN 101244297 8/2008
(Continued)

OTHER PUBLICATIONS

International Preliminary Report on Patentability, re PCT Application No. PCT/US 16/64467, dated Jun. 5, 2018.
(Continued)

*Primary Examiner* — Nicolas A Arnett
(74) *Attorney, Agent, or Firm* — Knobbe Martens Olson & Bear, LLP

(57) ABSTRACT

An example of a method of enabling medical fluid transfer between a source container and a destination container can comprise the steps of providing a closed-system fluid transfer module comprising a first closeable, resealable medical connector and a second closeable, resealable medical connector, a multidirectional fluid control valve with a driving interface configured to interface with an electromechanical driver of an electronic medical fluid transfer device, and an intermediate container or an intermediate pumping region; and instructing a user to couple the closed-system fluid transfer module to the electronic medical fluid transfer device.

8 Claims, 21 Drawing Sheets

Related U.S. Application Data continuation of application No. PCT/US2016/064467, filed on Dec. 1, 2016.

(60) Provisional application No. 62/263,541, filed on Dec. 4, 2015, provisional application No. 62/360,900, filed on Jul. 11, 2016.

(51) Int. Cl.
*A61M 5/142* (2006.01)
*A61M 39/24* (2006.01)
*A61J 1/14* (2006.01)
*A61J 1/22* (2006.01)
*A61J 1/20* (2006.01)
*A61M 5/145* (2006.01)

(52) U.S. Cl.
CPC ............... *A61J 1/22* (2013.01); *A61J 3/002* (2013.01); *A61M 5/142* (2013.01); *A61M 39/24* (2013.01); *A61J 2200/30* (2013.01); *A61J 2200/70* (2013.01); *A61J 2200/76* (2013.01); *A61M 2005/14506* (2013.01); *A61M 2039/242* (2013.01)

(58) Field of Classification Search
CPC .... A61J 3/002; A61J 2200/76; A61J 2200/30; A61J 2200/70
See application file for complete search history.

(56) References Cited

U.S. PATENT DOCUMENTS

| | | | |
|---|---|---|---|
| 3,344,785 A * | 10/1967 | Hamilton | A61M 1/0062 137/625.47 |
| D222,956 S | 2/1972 | Sato | |
| D222,957 S | 2/1972 | Sato | |
| D236,163 S | 7/1975 | Manno | |
| 4,005,710 A | 2/1977 | Zeddies et al. | |
| 4,084,606 A | 4/1978 | Mittleman | |
| 4,190,048 A | 2/1980 | Sampson | |
| 4,262,671 A | 4/1981 | Kersten | |
| 4,306,705 A | 12/1981 | Svensson | |
| 4,336,802 A | 6/1982 | Stone et al. | |
| 4,367,736 A | 1/1983 | Gupton | |
| D268,206 S | 3/1983 | Kosako | |
| D268,284 S | 3/1983 | Manno et al. | |
| 4,397,335 A | 8/1983 | Doblar et al. | |
| 4,410,321 A | 10/1983 | Pearson et al. | |
| 4,423,741 A | 1/1984 | Levy | |
| 4,519,792 A | 5/1985 | Dawe | |
| 4,534,758 A | 8/1985 | Akers et al. | |
| 4,559,043 A | 12/1985 | Whitehouse et al. | |
| 4,561,856 A | 12/1985 | Cochran | |
| 4,666,429 A | 5/1987 | Stone | |
| 4,670,007 A | 6/1987 | Wheeldon et al. | |
| 4,683,916 A | 8/1987 | Raines | |
| 4,755,172 A | 7/1988 | Baldwin | |
| 4,759,756 A | 7/1988 | Forman et al. | |
| 4,768,568 A | 9/1988 | Fournier et al. | |
| 4,778,450 A | 10/1988 | Kamen | |
| 4,819,684 A | 4/1989 | Zaugg et al. | |
| 4,863,429 A | 9/1989 | Baldwin | |
| D305,165 S | 12/1989 | Rudolph et al. | |
| 4,922,975 A | 5/1990 | Polaschegg | |
| 4,936,841 A | 6/1990 | Aoki et al. | |
| 4,969,874 A | 11/1990 | Michel et al. | |
| 4,972,876 A | 11/1990 | Kabata et al. | |
| 4,976,590 A | 12/1990 | Baldwin | |
| 4,995,268 A | 2/1991 | Ash et al. | |
| 5,024,347 A | 6/1991 | Baldwin | |
| 5,037,390 A | 8/1991 | Raines et al. | |
| 5,114,580 A | 5/1992 | Ahmad et al. | |
| D328,952 S | 8/1992 | Arioka | |
| 5,176,658 A | 1/1993 | Ranford | |
| 5,224,937 A | 7/1993 | van der Heiden et al. | |
| 5,256,155 A | 10/1993 | Yerlikaya et al. | |
| 5,288,290 A | 2/1994 | Brody | |
| 5,300,044 A | 4/1994 | Classey et al. | |
| D348,101 S | 6/1994 | Poli et al. | |
| 5,334,211 A | 8/1994 | Shiber | |
| 5,336,201 A | 8/1994 | von der Decken | |
| D352,778 S | 11/1994 | Irvin | |
| 5,378,231 A | 1/1995 | Johnson et al. | |
| 5,405,333 A | 4/1995 | Richmond | |
| 5,423,791 A | 6/1995 | Bartlett | |
| 5,431,201 A | 6/1995 | Torchia et al. | |
| 5,439,451 A | 8/1995 | Collinson et al. | |
| 5,466,220 A | 11/1995 | Brenneman | |
| 5,609,572 A | 3/1997 | Lang | |
| 5,645,538 A | 7/1997 | Richmond | |
| 5,647,845 A | 7/1997 | Haber et al. | |
| 5,678,346 A | 10/1997 | Leinsing | |
| 5,685,866 A | 11/1997 | Lopez | |
| 5,776,345 A | 7/1998 | Truitt et al. | |
| 5,782,816 A | 7/1998 | Werschmidt et al. | |
| 5,807,312 A | 9/1998 | Dzwonkiewicz | |
| 5,810,792 A | 9/1998 | Fangrow, Jr. et al. | |
| 5,871,110 A | 2/1999 | Grimard et al. | |
| 5,871,500 A | 2/1999 | Jepson et al. | |
| D408,079 S | 4/1999 | Ellis | |
| 5,897,526 A | 4/1999 | Vaillancourt | |
| 5,904,666 A | 5/1999 | DeDecker et al. | |
| 5,935,106 A | 8/1999 | Olsen | |
| 5,947,951 A | 9/1999 | Ortiz et al. | |
| 5,968,014 A | 10/1999 | Neftel et al. | |
| 5,989,237 A | 11/1999 | Fowles et al. | |
| 6,059,747 A | 5/2000 | Bruggeman et al. | |
| 6,110,153 A | 8/2000 | Davis et al. | |
| RE36,871 E | 9/2000 | Epstein et al. | |
| 6,123,685 A | 9/2000 | Reynolds | |
| 6,132,404 A | 10/2000 | Lopez | |
| 6,152,900 A | 11/2000 | Mayer | |
| 6,179,823 B1 | 1/2001 | Niedospial, Jr. | |
| 6,193,675 B1 | 2/2001 | Kraus et al. | |
| 6,202,708 B1 | 3/2001 | Bynum | |
| 6,221,041 B1 | 4/2001 | Russo | |
| 6,245,048 B1 | 6/2001 | Fangrow, Jr. et al. | |
| 6,287,289 B1 | 9/2001 | Niedospial, Jr. | |
| 6,302,864 B1 | 10/2001 | Nowosielski | |
| 6,425,497 B1 | 7/2002 | Chu et al. | |
| 6,474,375 B2 | 11/2002 | Spero et al. | |
| 6,485,472 B1 | 11/2002 | Richmond | |
| 6,551,299 B2 | 4/2003 | Miyoshi et al. | |
| 6,558,365 B2 | 5/2003 | Zinger et al. | |
| 6,572,256 B2 | 6/2003 | Seaton et al. | |
| 6,585,229 B2 | 7/2003 | Cote, Sr. et al. | |
| 6,590,167 B2 | 7/2003 | Clare | |
| 6,599,273 B1 | 7/2003 | Lopez | |
| 6,623,455 B2 | 9/2003 | Small et al. | |
| 6,629,956 B1 | 10/2003 | Polidoro et al. | |
| 6,651,956 B2 | 11/2003 | Miller | |
| 6,663,586 B2 | 12/2003 | Verkaart et al. | |
| 6,689,108 B2 | 2/2004 | Lavi et al. | |
| 6,699,230 B2 | 3/2004 | Jaafar et al. | |
| 6,726,672 B1 | 4/2004 | Hanly et al. | |
| 6,793,651 B1 | 9/2004 | Bennett et al. | |
| 6,813,868 B2 | 11/2004 | Baldwin et al. | |
| 6,854,620 B2 | 2/2005 | Ramet | |
| 6,908,459 B2 | 6/2005 | Harding et al. | |
| 6,915,823 B2 | 7/2005 | Osborne et al. | |
| 6,948,522 B2 | 9/2005 | Newbrough et al. | |
| 6,953,450 B2 | 10/2005 | Baldwin et al. | |
| 6,985,870 B2 | 1/2006 | Martucci et al. | |
| 6,991,002 B2 | 1/2006 | Osborne et al. | |
| 6,994,315 B2 | 2/2006 | Ryan et al. | |
| 6,997,917 B2 | 2/2006 | Niedospial, Jr. et al. | |
| 7,017,623 B2 | 3/2006 | Tribble et al. | |
| 7,086,431 B2 | 8/2006 | D'Antonio et al. | |
| 7,117,902 B2 | 10/2006 | Osborne | |
| 7,128,105 B2 | 10/2006 | Tribble et al. | |
| 7,163,035 B2 | 1/2007 | Khan et al. | |
| 7,175,615 B2 | 2/2007 | Hanly et al. | |
| 7,194,336 B2 | 3/2007 | DiGianfilippo et al. | |

(56) References Cited

U.S. PATENT DOCUMENTS

| | | | |
|---|---|---|---|
| 7,317,967 B2 | 1/2008 | DiGianfilippo et al. | |
| 7,343,224 B2 | 3/2008 | DiGianfilippo et al. | |
| 7,343,943 B2 | 3/2008 | Khan et al. | |
| 7,351,226 B1 | 4/2008 | Herskowitz | |
| 7,354,426 B2 | 4/2008 | Young | |
| 7,392,638 B2 | 7/2008 | Baldwin et al. | |
| 7,396,051 B2 | 7/2008 | Baldwin et al. | |
| 7,398,183 B2 | 7/2008 | Holland et al. | |
| 7,398,802 B2 * | 7/2008 | Baker | A61J 1/2089 141/27 |
| 7,418,981 B2 | 9/2008 | Baker et al. | |
| 7,442,186 B2 | 10/2008 | Blomquist | |
| 7,454,314 B2 | 11/2008 | Holland et al. | |
| 7,488,311 B2 | 2/2009 | Domkowski et al. | |
| 7,499,581 B2 | 3/2009 | Tribble | |
| 7,527,619 B2 | 5/2009 | Domkowski et al. | |
| 7,530,974 B2 | 5/2009 | Domkowski et al. | |
| 7,538,858 B2 | 5/2009 | Mackey | |
| D594,120 S | 6/2009 | Berberich et al. | |
| D596,291 S | 7/2009 | Berberich et al. | |
| 7,566,326 B2 | 7/2009 | Duchon et al. | |
| 7,590,021 B2 | 9/2009 | Michalak et al. | |
| 7,610,115 B2 | 10/2009 | Rob et al. | |
| 7,632,261 B2 | 12/2009 | Zinger et al. | |
| 7,654,976 B2 | 2/2010 | Peterson et al. | |
| 7,681,606 B2 | 3/2010 | Khan et al. | |
| D616,092 S | 5/2010 | Domkowski et al. | |
| 7,717,897 B2 | 5/2010 | Burg et al. | |
| D620,108 S | 7/2010 | Eitenmueller et al. | |
| 7,758,560 B2 | 7/2010 | Connell et al. | |
| 7,789,850 B2 | 9/2010 | Roger | |
| 7,814,731 B2 | 10/2010 | Bender et al. | |
| 7,850,051 B2 | 12/2010 | Py et al. | |
| 7,867,215 B2 | 1/2011 | Akerlund et al. | |
| 7,882,863 B2 * | 2/2011 | Pestotnik | A61J 1/2089 141/27 |
| 7,895,053 B2 | 2/2011 | Holland et al. | |
| 7,900,658 B2 | 3/2011 | Osborne et al. | |
| 7,913,720 B2 | 3/2011 | Tribble et al. | |
| 7,963,954 B2 | 6/2011 | Kavazov | |
| 7,967,202 B2 | 6/2011 | Durrell et al. | |
| 7,981,381 B2 | 7/2011 | Lurvey et al. | |
| 7,997,304 B2 * | 8/2011 | Ranalletta | B65B 3/003 141/104 |
| 8,034,041 B2 | 10/2011 | Domkowski et al. | |
| 8,065,161 B2 | 11/2011 | Howard et al. | |
| 8,075,545 B2 | 12/2011 | Moy et al. | |
| 8,091,727 B2 | 1/2012 | Domkowski | |
| 8,091,860 B2 | 1/2012 | Thompson et al. | |
| 8,104,644 B2 | 1/2012 | Py et al. | |
| 8,140,351 B2 | 3/2012 | Tribble et al. | |
| 8,141,601 B2 | 3/2012 | Fehr et al. | |
| 8,241,265 B2 | 3/2012 | Moy et al. | |
| 8,151,835 B2 | 4/2012 | Khan et al. | |
| 8,162,903 B2 | 4/2012 | Reilly et al. | |
| 8,162,914 B2 | 4/2012 | Kraushaar et al. | |
| 8,162,915 B2 | 4/2012 | Brandenburger et al. | |
| D660,423 S | 5/2012 | Hermle | |
| 8,172,823 B2 | 5/2012 | Rondeau et al. | |
| 8,197,459 B2 | 6/2012 | Jansen et al. | |
| 8,206,367 B2 | 6/2012 | Warren et al. | |
| D664,647 S | 7/2012 | Becker | |
| D664,648 S | 7/2012 | Becker | |
| D664,649 S | 7/2012 | Becker | |
| 8,216,207 B2 | 7/2012 | Moy et al. | |
| 8,220,504 B2 | 7/2012 | Hartman et al. | |
| 8,221,382 B2 | 7/2012 | Moy et al. | |
| 8,225,824 B2 | 7/2012 | Eliuk et al. | |
| 8,225,826 B2 | 7/2012 | Horppu et al. | |
| 8,231,567 B2 | 7/2012 | Tennican et al. | |
| 8,267,912 B2 | 9/2012 | Ferris | |
| 8,287,513 B2 | 10/2012 | Ellstrom et al. | |
| 8,328,082 B1 | 12/2012 | Bochenko et al. | |
| 8,336,587 B2 | 12/2012 | Rosenquist et al. | |
| 8,353,318 B2 | 1/2013 | Ranalletta et al. | |
| 8,356,644 B2 | 1/2013 | Chong et al. | |
| 8,356,645 B2 | 1/2013 | Chong et al. | |
| 8,357,137 B2 | 1/2013 | Yandell | |
| 8,374,887 B1 | 2/2013 | Alexander | |
| 8,380,536 B2 | 2/2013 | Howard et al. | |
| 8,381,776 B2 | 2/2013 | Horppu | |
| 8,382,696 B2 | 2/2013 | Beiriger et al. | |
| 8,403,905 B2 | 3/2013 | Yow | |
| 8,409,165 B2 | 4/2013 | Niedospial, Jr. et al. | |
| 8,414,554 B2 | 4/2013 | Garfield et al. | |
| 8,425,487 B2 | 4/2013 | Beiriger et al. | |
| 8,430,859 B2 | 4/2013 | McConnell | |
| 8,449,521 B2 | 5/2013 | Thorne, Jr. et al. | |
| 8,506,548 B2 | 8/2013 | Okiyama | |
| 8,522,832 B2 | 9/2013 | Lopez et al. | |
| 8,543,416 B2 | 9/2013 | Palmroos et al. | |
| 8,551,037 B2 | 10/2013 | Suchecki et al. | |
| 8,562,583 B2 | 10/2013 | Akerlund et al. | |
| 8,567,235 B2 | 10/2013 | Bojan et al. | |
| 8,562,584 B2 | 11/2013 | Beiriger et al. | |
| 8,602,067 B2 | 12/2013 | Kuhni et al. | |
| 8,608,723 B2 | 12/2013 | Lev | |
| 8,622,985 B2 | 1/2014 | Ellstrom | |
| 8,636,720 B2 | 1/2014 | Truitt et al. | |
| 8,660,860 B2 | 2/2014 | Wehba et al. | |
| 8,911,421 B2 | 2/2014 | Domkowski et al. | |
| 8,679,075 B2 | 3/2014 | Lurvey et al. | |
| 8,684,994 B2 | 4/2014 | Lev et al. | |
| 8,700,421 B2 | 4/2014 | Feng et al. | |
| 8,701,696 B2 | 4/2014 | Guala | |
| 8,702,675 B2 | 4/2014 | Imai | |
| 8,720,496 B2 | 5/2014 | Huwiler et al. | |
| 8,721,612 B2 | 5/2014 | Moy et al. | |
| 8,721,614 B2 | 5/2014 | Takemoto et al. | |
| 8,721,627 B2 | 5/2014 | Alpert | |
| 8,753,325 B2 | 6/2014 | Lev et al. | |
| 8,763,798 B2 | 7/2014 | Paul | |
| 8,795,231 B2 | 8/2014 | Chong et al. | |
| 8,801,689 B2 | 8/2014 | Moy et al. | |
| 8,821,436 B2 | 9/2014 | Mosler et al. | |
| 8,834,444 B2 | 9/2014 | Domkowski | |
| 8,852,147 B2 | 10/2014 | Callan et al. | |
| 8,863,788 B2 * | 10/2014 | Ranalletta | B65B 3/003 141/104 |
| 8,864,725 B2 | 10/2014 | Ranalletta et al. | |
| 8,864,737 B2 | 10/2014 | Hasegawa et al. | |
| 8,870,832 B2 | 10/2014 | Raday et al. | |
| 8,882,739 B2 | 11/2014 | Domkowski et al. | |
| D721,803 S | 1/2015 | Dubach | |
| 8,926,554 B2 | 1/2015 | Okuda et al. | |
| 8,958,112 B2 | 2/2015 | Matsui et al. | |
| D724,198 S | 3/2015 | Oostman et al. | |
| 8,973,622 B2 | 3/2015 | Lopez et al. | |
| 8,979,792 B2 | 3/2015 | Lev et al. | |
| 9,043,019 B2 | 5/2015 | Eliuk et al. | |
| 9,056,164 B2 | 6/2015 | Tate et al. | |
| 9,057,363 B2 | 6/2015 | Capone | |
| 9,057,370 B2 | 6/2015 | Mundt et al. | |
| 9,060,923 B2 | 6/2015 | Hossainy | |
| 9,061,130 B2 | 6/2015 | Truitt et al. | |
| 9,079,686 B2 | 7/2015 | Domkowski et al. | |
| 9,089,474 B2 | 7/2015 | Cederschiöld | |
| 9,101,717 B2 | 8/2015 | Mansour et al. | |
| 9,114,242 B2 | 8/2015 | Fangrow, Jr. et al. | |
| 9,123,077 B2 | 9/2015 | Silkaitis et al. | |
| 9,132,062 B2 | 9/2015 | Fangrow | |
| 9,132,063 B2 | 9/2015 | Lev et al. | |
| 9,139,316 B2 | 9/2015 | Husnu et al. | |
| 9,144,646 B2 | 9/2015 | Barron, III et al. | |
| 9,149,576 B2 | 10/2015 | Bullington et al. | |
| 9,198,832 B2 | 12/2015 | Moy et al. | |
| 9,211,231 B2 | 12/2015 | Mansour et al. | |
| 9,212,762 B2 | 12/2015 | Duncan | |
| 9,227,048 B2 | 1/2016 | Frattini | |
| 9,242,039 B2 | 1/2016 | Valk et al. | |
| 9,270,890 B2 | 2/2016 | Okuma et al. | |
| 9,345,640 B2 | 5/2016 | Mosler et al. | |
| 9,345,641 B2 | 5/2016 | Krause et al. | |
| 9,345,643 B2 | 5/2016 | Okiyama | |

(56) References Cited

U.S. PATENT DOCUMENTS

| | | |
|---|---|---|
| 9,381,135 B2 | 7/2016 | Reynolds et al. |
| 9,381,137 B2 | 7/2016 | Garfield et al. |
| 9,381,296 B2 | 7/2016 | Arrizza et al. |
| 9,393,362 B2 | 7/2016 | Cozmi et al. |
| 9,402,786 B2 | 8/2016 | Petrone |
| 9,481,477 B2 * | 11/2016 | Kjar .................. C12M 23/40 |
| D774,192 S | 12/2016 | Fuchs |
| D775,325 S | 12/2016 | Larson et al. |
| 9,511,989 B2 | 12/2016 | Lopez et al. |
| 9,561,893 B2 | 2/2017 | Root et al. |
| 9,572,923 B2 | 2/2017 | Howard et al. |
| 9,629,955 B2 | 4/2017 | Bresina et al. |
| 9,744,102 B2 | 8/2017 | Kubo |
| 9,775,778 B2 | 10/2017 | Qiu et al. |
| 9,801,787 B2 | 10/2017 | Py |
| D803,396 S | 11/2017 | Oberkircher et al. |
| 9,827,163 B2 | 11/2017 | Lopez et al. |
| D804,651 S | 12/2017 | Loonan |
| 9,849,236 B2 * | 12/2017 | Hachey .................. A61M 39/22 |
| 9,883,987 B2 * | 2/2018 | Lopez ................ A61M 5/14228 |
| 9,931,276 B2 | 4/2018 | Lopez et al. |
| 10,188,849 B2 | 1/2019 | Fangrow |
| 2001/0029360 A1 | 10/2001 | Miyoshi et al. |
| 2002/0017328 A1 | 2/2002 | Loo |
| 2002/0095121 A1 | 7/2002 | Norton et al. |
| 2002/0179544 A1 | 12/2002 | Johnson et al. |
| 2002/0189712 A1 | 12/2002 | Safabash |
| 2003/0023226 A1 | 1/2003 | Lopez |
| 2003/0153895 A1 | 8/2003 | Leinsing |
| 2003/0236500 A1 | 12/2003 | Scheu |
| 2004/0035743 A1 | 2/2004 | Tighe et al. |
| 2004/0087888 A1 | 5/2004 | Digianfilippo et al. |
| 2004/0116891 A1 | 6/2004 | Curutcharry |
| 2004/0118477 A1 | 6/2004 | Desmond |
| 2004/0225274 A1 | 11/2004 | Jansen et al. |
| 2005/0033260 A1 | 2/2005 | Kubo et al. |
| 2005/0096627 A1 | 5/2005 | Howard |
| 2005/0131357 A1 | 6/2005 | Denton et al. |
| 2005/0230575 A1 | 10/2005 | Zelenski et al. |
| 2005/0252572 A1 | 11/2005 | Khan et al. |
| 2005/0252574 A1 | 11/2005 | Khan et al. |
| 2005/0278194 A1 | 12/2005 | Holland et al. |
| 2006/0064053 A1 | 3/2006 | Bollish et al. |
| 2006/0089854 A1 | 4/2006 | Holland et al. |
| 2006/0089855 A1 | 4/2006 | Holland et al. |
| 2006/0100907 A1 | 5/2006 | Holland et al. |
| 2006/0259195 A1 | 11/2006 | Eliuk et al. |
| 2007/0007478 A1 | 1/2007 | Leinsing et al. |
| 2007/0088252 A1 * | 4/2007 | Pestotnik .............. A61J 1/2089 604/82 |
| 2007/0088313 A1 | 4/2007 | Zinger et al. |
| 2007/0106244 A1 | 5/2007 | Mosler et al. |
| 2007/0214003 A1 | 9/2007 | Holland et al. |
| 2007/0244447 A1 | 10/2007 | Capitaine et al. |
| 2007/0287953 A1 | 12/2007 | Ziv et al. |
| 2008/0065006 A1 | 3/2008 | Roger et al. |
| 2008/0086094 A1 | 4/2008 | Peters |
| 2008/0114328 A1 * | 5/2008 | Doherty ................ A61J 1/2096 604/414 |
| 2008/0125897 A1 | 5/2008 | DiGianfilippo et al. |
| 2008/0169043 A1 | 7/2008 | Osborne |
| 2008/0169044 A1 | 7/2008 | Osborne et al. |
| 2008/0172024 A1 | 7/2008 | Yow |
| 2008/0177222 A1 | 7/2008 | De Marco et al. |
| 2008/0195416 A1 | 8/2008 | Tribble et al. |
| 2008/0199353 A1 | 8/2008 | Mlodzinski et al. |
| 2008/0269680 A1 | 10/2008 | Ibranyan et al. |
| 2008/0287920 A1 | 11/2008 | Fangrow et al. |
| 2009/0012449 A1 | 1/2009 | Lee et al. |
| 2009/0050216 A1 | 2/2009 | Trocki et al. |
| 2009/0067973 A1 | 3/2009 | Eliuk et al. |
| 2009/0069743 A1 | 3/2009 | Krishnamoorthy et al. |
| 2009/0082649 A1 | 3/2009 | Muller et al. |
| 2009/0088687 A1 | 4/2009 | Yardimci et al. |
| 2009/0099547 A1 | 4/2009 | Radmer |
| 2009/0101576 A1 | 4/2009 | Rohde et al. |
| 2009/0126825 A1 | 5/2009 | Eliuk et al. |
| 2009/0135196 A1 | 5/2009 | Holland et al. |
| 2009/0145509 A1 | 6/2009 | Baker et al. |
| 2009/0149743 A1 * | 6/2009 | Barron .................. A61M 5/007 600/431 |
| 2009/0163860 A1 | 6/2009 | Patrick et al. |
| 2009/0177149 A1 | 7/2009 | Childers et al. |
| 2009/0198215 A1 | 8/2009 | Chong et al. |
| 2009/0254031 A1 | 10/2009 | Lee |
| 2009/0270832 A1 | 10/2009 | Vancaillie et al. |
| 2009/0306621 A1 * | 12/2009 | Thome, Jr. .......... A61M 5/1408 604/500 |
| 2010/0024904 A1 | 2/2010 | Hoffman et al. |
| 2010/0049157 A1 | 2/2010 | Fangrow |
| 2010/0121246 A1 | 5/2010 | Peters et al. |
| 2010/0130933 A1 | 5/2010 | Holland et al. |
| 2010/0245056 A1 | 9/2010 | Braun et al. |
| 2010/0276034 A1 | 11/2010 | Gonnelli et al. |
| 2010/0280430 A1 | 11/2010 | Caleffi et al. |
| 2010/0286606 A1 | 11/2010 | Ding |
| 2011/0062703 A1 | 3/2011 | Lopez et al. |
| 2011/0087164 A1 | 4/2011 | Mosler et al. |
| 2011/0152757 A1 | 6/2011 | Beck et al. |
| 2011/0175347 A1 | 7/2011 | Okiyama |
| 2011/0178493 A1 | 7/2011 | Okiyama |
| 2011/0196304 A1 | 8/2011 | Kramer et al. |
| 2012/0167914 A1 | 1/2012 | Stroup |
| 2012/0067429 A1 | 3/2012 | Mosler et al. |
| 2012/0109077 A1 | 5/2012 | Ryan |
| 2012/0123298 A1 | 5/2012 | Mendels et al. |
| 2012/0157914 A1 | 6/2012 | Stroup |
| 2012/0302986 A1 | 11/2012 | Brem et al. |
| 2013/0006214 A1 | 1/2013 | Garfield et al. |
| 2013/0053815 A1 | 2/2013 | Mucientes et al. |
| 2013/0180618 A1 | 7/2013 | Py |
| 2013/0211332 A1 | 8/2013 | Beiriger et al. |
| 2013/0218121 A1 | 8/2013 | Waller et al. |
| 2013/0220484 A1 | 8/2013 | De Marco |
| 2014/0124087 A1 | 5/2014 | Anderson et al. |
| 2014/0135732 A1 | 5/2014 | Spronken et al. |
| 2014/0150925 A1 | 6/2014 | Sjogren et al. |
| 2014/0261727 A1 | 9/2014 | Mansour et al. |
| 2014/0261860 A1 | 9/2014 | Heath |
| 2014/0261877 A1 | 9/2014 | Ivosevic et al. |
| 2014/0263614 A1 | 9/2014 | Keefe et al. |
| 2014/0276386 A1 | 9/2014 | Mansour et al. |
| 2014/0276649 A1 | 9/2014 | Ivosevic et al. |
| 2014/0299221 A1 * | 10/2014 | Lopez ................ A61M 5/14228 141/1 |
| 2014/0323970 A1 | 10/2014 | Duncan |
| 2015/0000784 A1 | 1/2015 | Jamaledine |
| 2015/0008664 A1 | 1/2015 | Tachizaki |
| 2015/0025453 A1 | 1/2015 | Ledford et al. |
| 2015/0040987 A1 | 2/2015 | Reichert et al. |
| 2015/0040988 A1 | 2/2015 | Reichert et al. |
| 2015/0041531 A1 | 2/2015 | Vavala et al. |
| 2015/0045772 A1 | 2/2015 | Reichert et al. |
| 2015/0051751 A1 | 2/2015 | Kirschbaum et al. |
| 2015/0101707 A1 | 4/2015 | Ranalletta et al. |
| 2015/0119820 A1 | 4/2015 | Kanamoto |
| 2015/0123398 A1 | 5/2015 | Sanders et al. |
| 2015/0126958 A1 | 5/2015 | Sanders et al. |
| 2015/0133879 A1 | 5/2015 | Kanamoto et al. |
| 2015/0151041 A1 | 6/2015 | Yodfat et al. |
| 2015/0157536 A1 | 6/2015 | Qiu et al. |
| 2015/0161354 A1 | 6/2015 | Blomquist |
| 2015/0202382 A1 | 7/2015 | Juretich et al. |
| 2015/0202383 A1 | 7/2015 | Juretich et al. |
| 2015/0202384 A1 | 7/2015 | Juretich et al. |
| 2015/0202385 A1 | 7/2015 | Juretich et al. |
| 2015/0209230 A1 | 7/2015 | Lev et al. |
| 2015/0209233 A1 | 7/2015 | Fukuoka |
| 2015/0209495 A1 | 7/2015 | Biset et al. |
| 2015/0209510 A1 | 7/2015 | Burkhotz et al. |
| 2015/0209572 A1 | 7/2015 | Garfield et al. |
| 2015/0250680 A1 | 9/2015 | Browka et al. |
| 2015/0250681 A1 | 9/2015 | Lev et al. |
| 2015/0257977 A1 | 9/2015 | Bochenko et al. |

(56) References Cited

U.S. PATENT DOCUMENTS

| | | |
|---|---|---|
| 2015/0265500 A1 | 9/2015 | Russo et al. |
| 2015/0297451 A1 | 10/2015 | Mariei et al. |
| 2015/0297453 A1 | 10/2015 | Kim et al. |
| 2015/0297454 A1 | 10/2015 | Sanders et al. |
| 2015/0297456 A1 | 10/2015 | Mariei et al. |
| 2015/0297459 A1 | 10/2015 | Sanders et al. |
| 2015/0297460 A1 | 10/2015 | Mansour et al. |
| 2015/0297839 A1 | 10/2015 | Sanders et al. |
| 2015/0297881 A1 | 10/2015 | Sanders et al. |
| 2015/0314066 A1 | 11/2015 | Shimizu |
| 2015/0320992 A1 | 11/2015 | Bonnet et al. |
| 2015/0346013 A1 | 12/2015 | Feng et al. |
| 2015/0359709 A1 | 12/2015 | Kriheli et al. |
| 2015/0366758 A1 | 12/2015 | Noguchi et al. |
| 2016/0000653 A1 | 1/2016 | Kramer |
| 2016/0038373 A1 | 2/2016 | Ohlin |
| 2016/0038374 A1 | 2/2016 | Merhold et al. |
| 2016/0051446 A1 | 2/2016 | Lev et al. |
| 2016/0058667 A1 | 3/2016 | Kriheli |
| 2016/0081878 A1 | 3/2016 | Marks et al. |
| 2016/0081879 A1 | 3/2016 | Garfield et al. |
| 2016/0101020 A1 | 4/2016 | Guala |
| 2016/0114922 A1 | 4/2016 | Bonhora et al. |
| 2016/0136051 A1 | 5/2016 | Lavi |
| 2016/0136412 A1 | 5/2016 | McKinnon et al. |
| 2016/0158104 A1 | 6/2016 | Ali et al. |
| 2016/0206511 A1 | 7/2016 | Garfield et al. |
| 2016/0213568 A1 | 7/2016 | Mansour et al. |
| 2016/0213861 A1 | 7/2016 | Whitaker et al. |
| 2016/0213862 A1 | 7/2016 | Whitaker et al. |
| 2016/0250102 A1 | 9/2016 | Garfield et al. |
| 2016/0256632 A1 | 9/2016 | Fangrow |
| 2016/0262981 A1 | 9/2016 | Carrez et al. |
| 2016/0331893 A1 | 11/2016 | Yeh et al. |
| 2017/0007501 A1 | 1/2017 | Schuldt-Lieb et al. |
| 2017/0128666 A1 | 5/2017 | Davis |
| 2017/0129763 A1* | 5/2017 | Fangrow, Jr. ............ A61J 1/10 |
| 2017/0165435 A1 | 6/2017 | Green |
| 2017/0165436 A1 | 6/2017 | Haddad et al. |
| 2017/0274140 A1 | 9/2017 | Howard et al. |
| 2017/0354571 A1 | 12/2017 | David et al. |
| 2018/0055735 A1 | 3/2018 | Lopez |
| 2018/0161244 A1* | 6/2018 | Lopez ............... A61M 5/14228 |
| 2018/0177940 A1 | 6/2018 | Hachey |
| 2018/0207063 A1 | 7/2018 | Lopez |
| 2019/0021947 A1 | 1/2019 | Bomgaars et al. |

FOREIGN PATENT DOCUMENTS

| | | |
|---|---|---|
| CN | 106860003 A | 6/2017 |
| CN | 107198658 A | 9/2017 |
| CN | 108210332 A | 6/2018 |
| DE | 20 2004 014 868 | 11/2004 |
| EP | 0 521 460 B1 | 9/1995 |
| EP | 0 974 330 | 1/2000 |
| EP | 1 563 819 | 8/2005 |
| EP | 1 997 471 | 12/2008 |
| EP | 3 375 427 A1 | 9/2018 |
| JP | 55-173339 | 12/1980 |
| JP | 56-95247 A | 8/1981 |
| JP | 62-189072 A | 8/1987 |
| JP | 06-343706 | 12/1994 |
| JP | 10-118158 A | 5/1998 |
| JP | 2001-190689 A | 7/2001 |
| JP | 2002-238979 A | 8/2002 |
| JP | 2002-355318 | 12/2002 |
| JP | 2003-144546 | 5/2003 |
| JP | 2003-225305 A | 8/2003 |
| JP | 2007-215775 A | 8/2007 |
| KR | 10-1095961 B1 | 12/2011 |
| KR | 10-1574194 B1 | 12/2015 |
| WO | WO 1997/14493 | 4/1997 |
| WO | WO 1998/23353 | 6/1998 |
| WO | WO 1999/63547 | 12/1999 |
| WO | WO 2001/03757 | 1/2001 |
| WO | WO 2001/039874 | 6/2001 |
| WO | WO 2005/041846 | 5/2005 |
| WO | WO 2005/110007 | 11/2005 |
| WO | WO 2005/123162 | 12/2005 |
| WO | WO 2007/033013 | 3/2007 |
| WO | WO 2007/061424 | 5/2007 |
| WO | WO 2007/079305 | 7/2007 |
| WO | WO 2007/148708 | 12/2007 |
| WO | WO 2008/128074 | 10/2008 |
| WO | WO 2009/060419 | 5/2009 |
| WO | WO 2009/130147 | 10/2009 |
| WO | WO 2011/012313 | 2/2011 |
| WO | WO 2011/058545 | 5/2011 |
| WO | WO 2011/058548 | 5/2011 |
| WO | WO 2011/091542 | 8/2011 |
| WO | WO 2011/091543 | 8/2011 |
| WO | WO 2011/104711 | 9/2011 |
| WO | WO 2011/104712 | 9/2011 |
| WO | WO 2011/150037 | 12/2011 |
| WO | WO 2012/119225 | 9/2012 |
| WO | WO 2014/122843 | 8/2014 |
| WO | WO 2014/126473 | 8/2014 |
| WO | WO 2014/177347 | 11/2014 |
| WO | WO 2014/181320 | 11/2014 |
| WO | WO 2015/029020 | 3/2015 |
| WO | WO 2018/009996 | 1/2018 |
| WO | WO 2019/018195 | 1/2019 |

OTHER PUBLICATIONS

U.S. Appl. No. 15/933,954, filed Mar. 23, 2018, Lopez et al.
U.S. Appl. No. 29/571,547, Jul. 19, 2016, Shauver et al.
U.S. Appl. No. 29/586,575, filed Dec. 5, 2016, Fangrow.
Abbott Laboratories, "Abbott MedNet Software," Installation and User Guide in 156 pages, Copyright 2006. (Part 1—pp. 1-78).
Abbott Laboratories, "Abbott MedNet Software," Installation and User Guide, in 156 pages, Copyright 2006. (Part 2—pp. 79-156).
Autoyec 50, from KRZ, Dec. 6, 2007.
B. Braun Medical Inc. Two-Bag Irrigation Set, Two Non-vented Spikes, dated Jul. 2012, in 1 page.
BioExpert International Inc., Company overview, credentials for Rabih Jamaleddine, Nabil Kereknawi, and Danica Robillard Corso, copyright 2010 BioExpert International Inc. in 3 pages [retrieved on Jan. 6, 2015; Publication Date Unknown]; accessed on the world wide web at http://bioexpert.ca/about.html.
Cato (Computer Aided Therapy for Oncology)—Reference Manual—Vienna, May 2005, 255 pgs.
Clearlink Needleless IV Access System, dated Aug. 2007, in 2 pages.
CytoCare, by Health Robotics, Brochure, Date Unknown, downloaded on May 25, 2012 from http://www.health-robotics.com/smartedit/downloads/en/cylocare7.pdf, 6 pages.
Exacta-Mix 2400, from Baxa, which appears to have a date of 2007, 2 pages.
Flickinger, Bruce, "Misperceptions Cloud the Issue of Sterile Drug Compounding," Jun. 2007.
Fox Brent I., "Pharmacy Automation and Technology: Automated intravenous Preparation: Robots for the Pharmacy," Hospital Pharmacy, vol. 44, Mar. 2009, pp. 255-257.
Grifols International, S.A., "PHOCUS Rx, Remote IV Compounding Validation" product brochure and "Product Description Sheet" in 13 pages [Publication Date unknown but may be May 29, 2013].
Healthmark, "Hospital Medication Preparation, Packaging and Dispensing" in 1 page [retrieved on Jan. 6, 2015; Publication Date Unknown]; accessed on the world wide web at http://www.healthmark.ca/2-en-Hospital-Medication-Preparation-Packaging-and-Dispensing.html.
Healthmark, "Hospital Medication Preparation, Packaging and Dispensing," Chemo Drug Preparation/Administration in 2 pages [retrieved on Jan. 6, 2015; Publication Date Unknown]; accessed on the world wide web at http://wwwhealthmark.ca/2-36-88-Chemo-Drug-Preparation-Administration_en.html.

(56) References Cited

OTHER PUBLICATIONS

Healthrnark, "Hospital Medication Preparation, Packaging and Dispensing," Chemosphere, Sterile Chemo Compounding (Isolator) in 1 page [retrieved on Jan. 6, 2015; Publication Date Unknown]; accessed on the world wide web at http://www.healthmark.ca/2-36-10-ChemoSphere_en.html?ProduitID=244.

Healthrnark, "Hospital Medication Preparation, Packaging and Dispensing," Oncology Preparation and Administration in 1 page [retrieved on Jan. 6, 2015; Publication Date Unknown]; accessed on the world wide web at http://www.healthmark.ca/2-36-10-Company-PROFILEHospital-en.html.

Healthmark, "Hospital Medication Preparation, Packaging and Dispensing,"Phocus RX (Camera Verification System), Remote Rx Checking of admixtures in 2 pages [retrieved on Jan. 6, 2015; Publication Date Unknown]; accessed on the world wide web at http://www.healthmark.ca/2-36-10-PHOCUS-Rx-Camera-Verification-Syster-_en.html?ProduitID=229.

Healthmark, "New Product Items" in 1 page [retrieved on Jan. 6, 2015; Publication Date Unknown]; accessed on the world wide web at http://www.healthmark.ca/home.html.

Healthrnark, "Introducing the Precifill Dispensing Pump" product brochure in 2 pages [Publication Date Unknown].

Hospira,"Hospice MedNet Software Suite," IT Implementation Training Guide in 143 pages, Copyright 2006.

Hospira, "LifeCare PCA with Hospira MedNet Software," LifeCare PCA Technical Service Manual in 208 pages, Published 2007. (Part 1—pp. 1-104).

Hospira,"LifeCare PCA with Hospira MedNet Software," LifeCare PCA Technical Service Manual in 208 pages, Published 2007, (Part 2—pp. 105-208).

Integra Brochure, from Eurospital, Brochure acquired in Mar. 2012.

International Invitation to Pay Additional Fees (with cited art), re PCT Application No. PCT/US 16/64467, dated Jan. 25, 2017.

International Search Report and Written Opinion, re PCT Application No. PCT/US 16/64467, dated Apr. 5, 2017.

ISO/Tech Design, QC, Canada "Chemosphere," product brochure in 2 pages [Publication Date Unknown].

Machine transcription generated by YouTube taken from a video titled, "RIVA Robotic IV Automation," available at https://www.youtube.com/watch?v=GbLIBNIVIPv9Y, as allegedly published on Sep. 11, 2006.

Neo Care Medical Products; Product Catalog, dated Jun. 2008, in 38 pages.

Pinnacle TPN Management System, from B Braun, downloaded May 5, 2009 from http://www.bbraunusa.com/index.cfm?uuid=7386ADF065B05CD0D22AF700339AA4092, 1 page.

"Precifill," Trademark search (TESS) in 1 page, [retrieved on Jan. 6, 2015; Appliation Filing Date of Sep. 30, 2011]; accessed on the world wide web at http://tmsearch.uspto.gov/bin/showfield?f=doc&state=4807:gz67gx.3.1.

Product detail for "NAMIC® Closed Fluid Systems" from Navilyst Medical, downloaded on May 11, 2010 from http://www.navilystmedical.com/Products/index.cfm/9, 2 pages.

Product detail for "RapidFill™ Automated Syringe Filler," from Baxa, downloaded on Mar. 31, 2010 from http://www.baxa.com/PharmacyProducts/AutomatedFillingSystems/ProductDetail/?id=B1, 2 pages.

Product detail for "Summit Medical DirectFlow" micro infusion extension set from Summit Medical Technologies, downloaded on May 10, 2010 from http://summitmedtech.com/p6line.php, 1 page.

Richard Anders "RIVA Robotic IV Automation," available at https://www.youtube.com/watch?v=GbLIBNMPv9Y, as allegedly published Sep. 11, 2006.

Riva, downloaded in Apr. 2009 from http://www.rivasystem.com, 6 pages.

SmartSite Safety Disposabies, with copyright, notice dated 2004.

Smith, "Lifesaving Cancer Drugs May Put Workers' Lives at Risk," downloaded on Jul. 12, 2010 from http://www.msnbc.msn.com/id/38114586/ns/health-cancer, 7 pages.

Spiros—Closed Male Connector, published Jan. 22, 2008.

Technical Data sheet for Analog Amplifiers Type VA, models V8-C and V8-D, STM Sensors dated Dec. 2007, 4 pages.

Technical Data sheet for Through Beam Sensors Type G2, 1480 nm, STM Sensors dated Dec. 2009, 2 pages.

Technical Data sheet for Through Beam Sensors Type G2, 645 nm, STM Sensors dated Sep. 2008, 2 pages.

User Guide for medOC 1xx Basic, Neo Care Medical Products GmbH; Version Jun. 2008, 23 pages.

User Manual for med0C 3xx /6xx /8xx, Neo Care Medical Products GmbH, Version May 2008, 44 pages.

\* cited by examiner

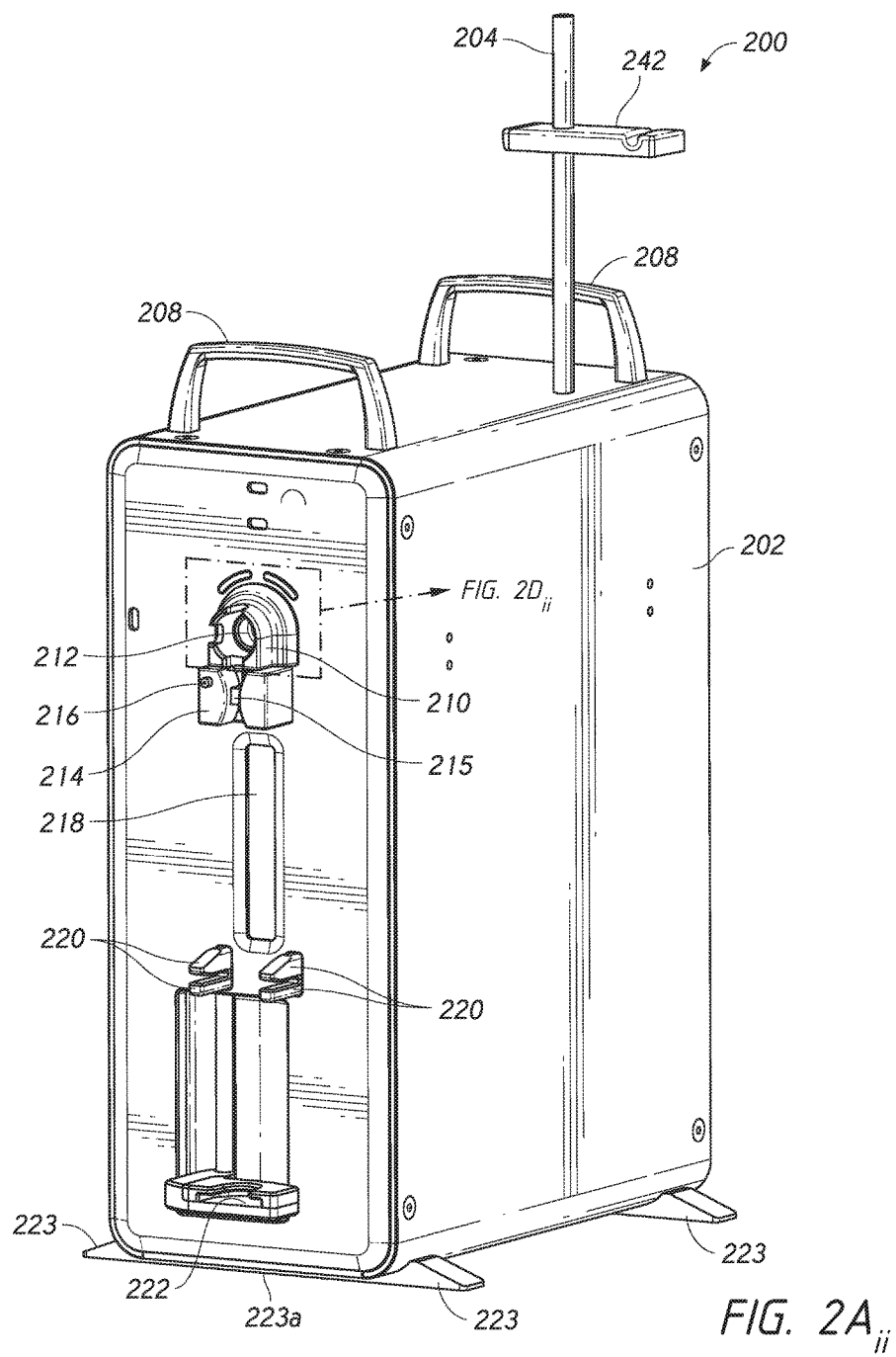
FIG. 2A_ii

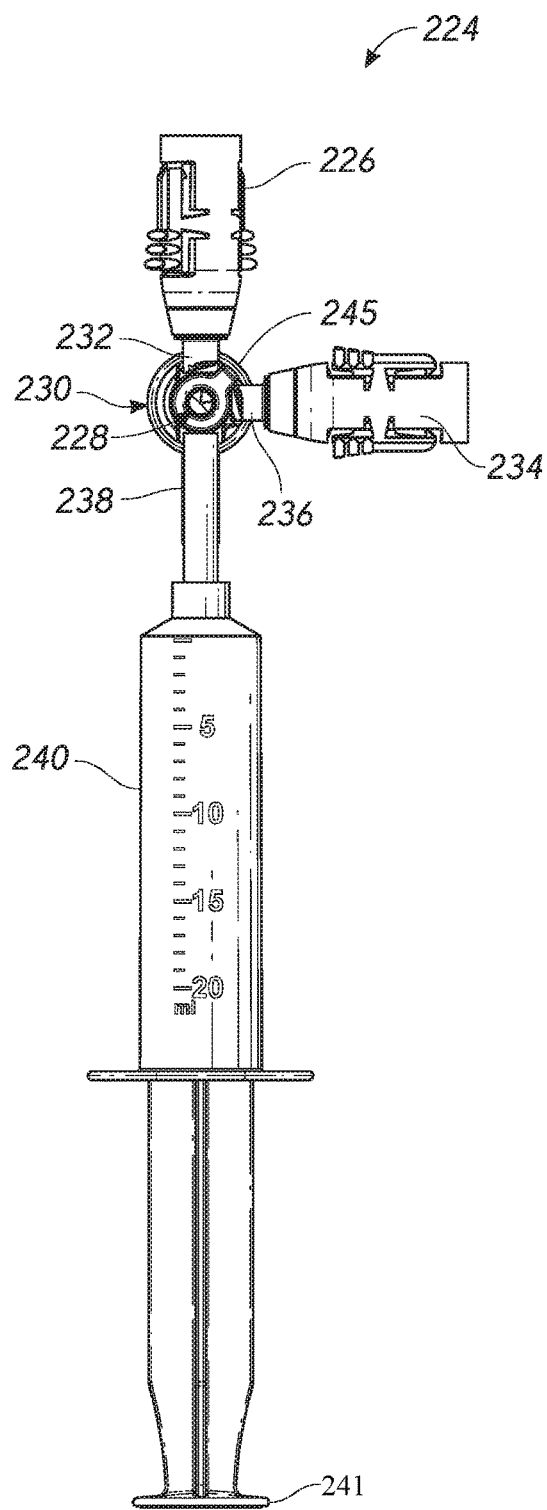
FIG. 2B_ii

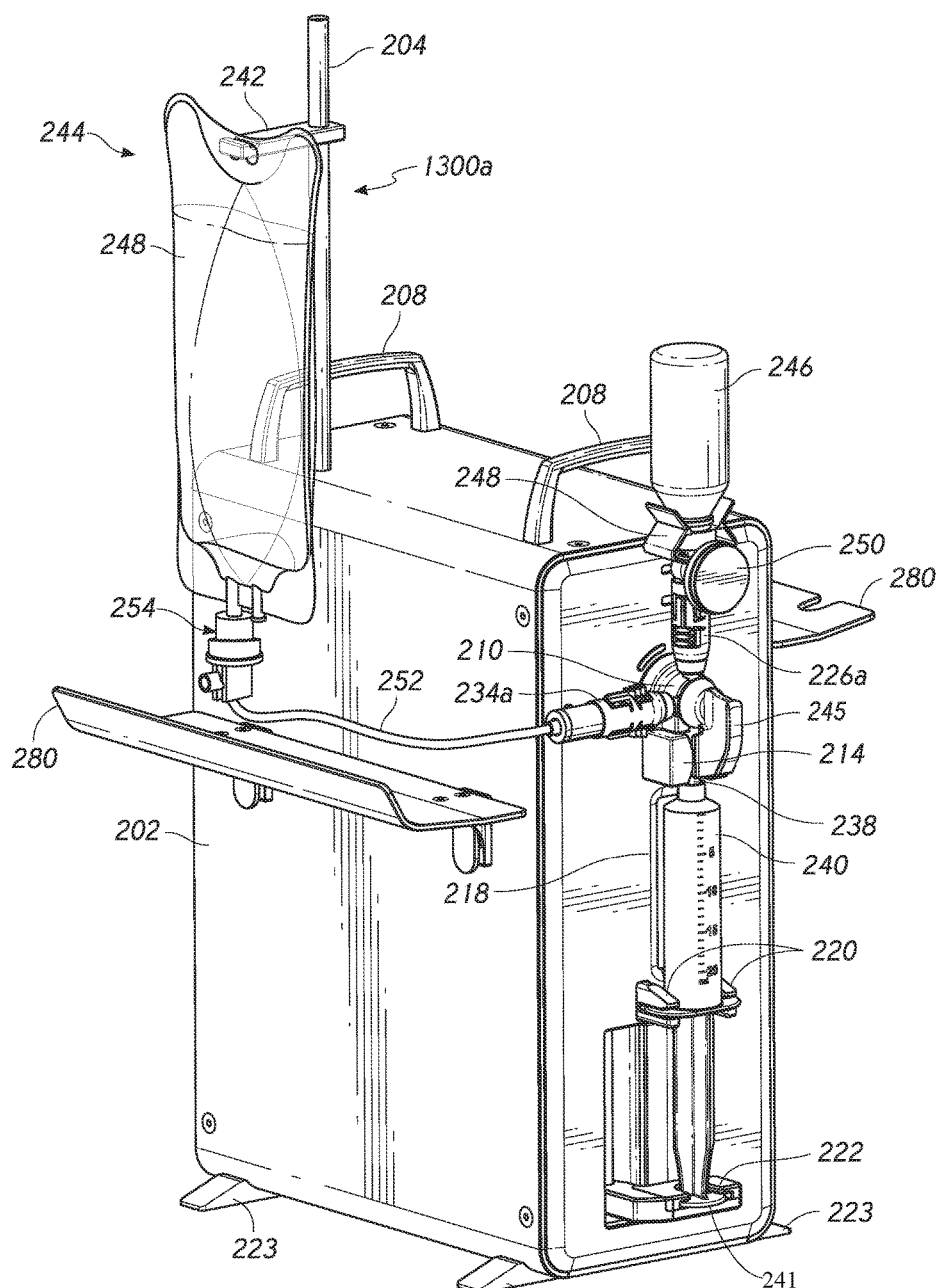
FIG. 2C_ii

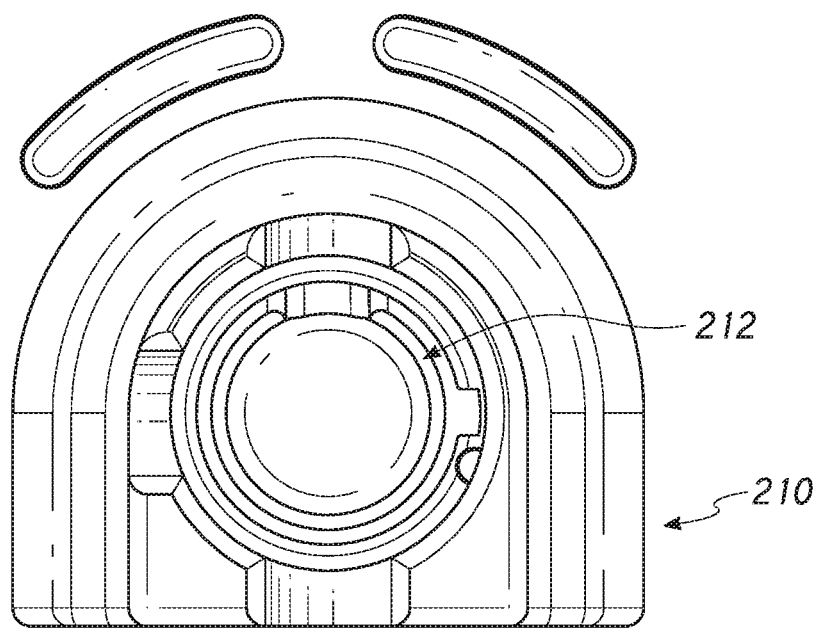
FIG. 2D$_{ii}$

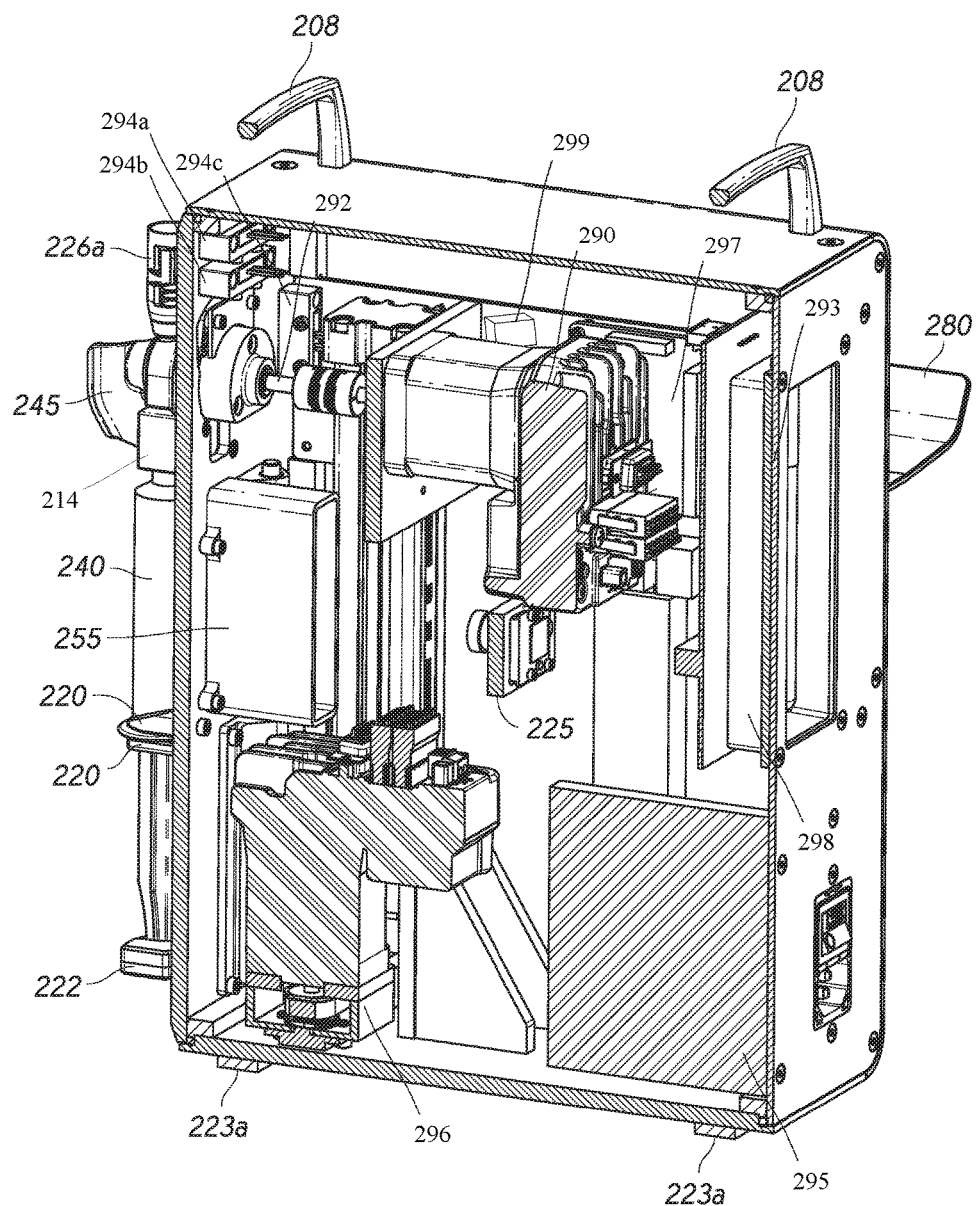
FIG. 2E$_{ii}$

*FIG. 3*

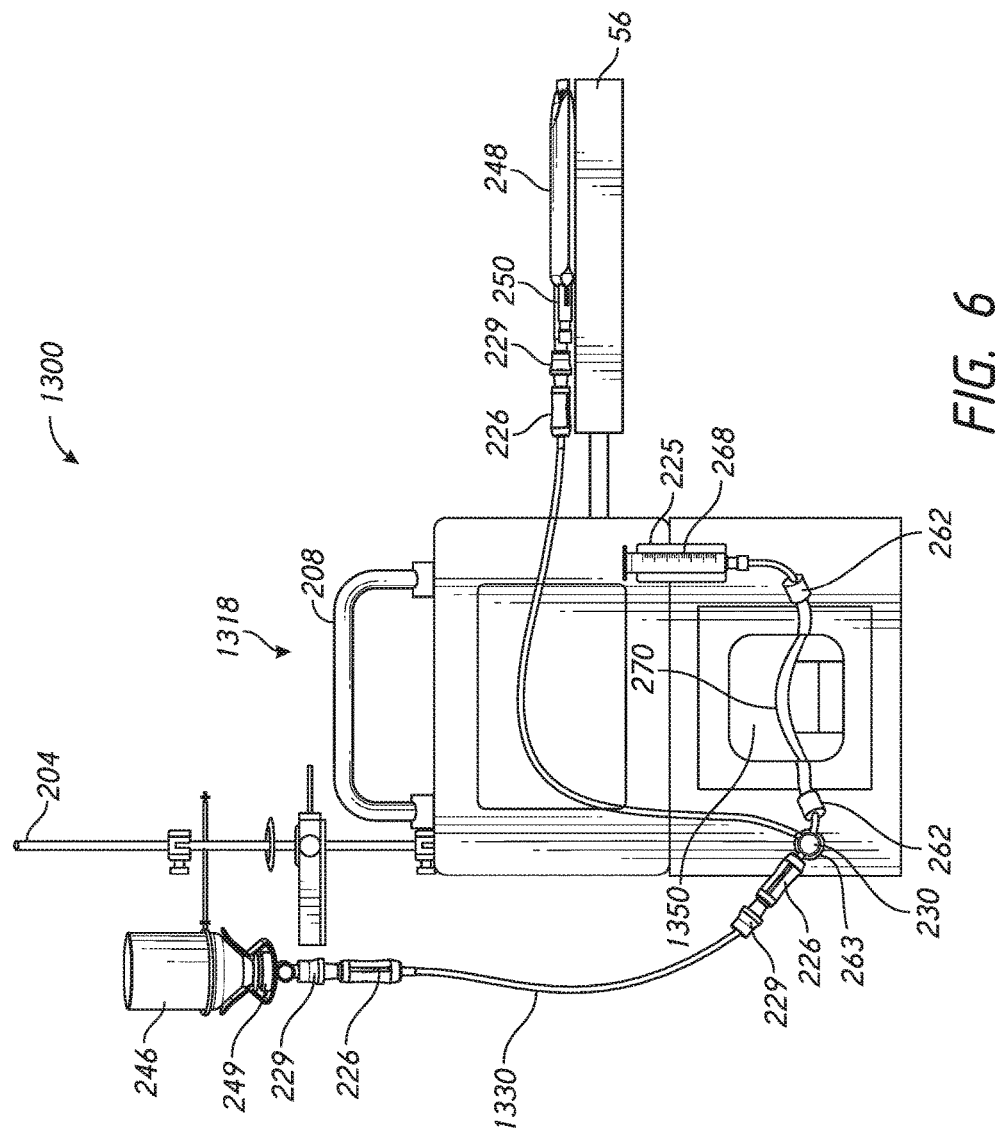

SYSTEMS, METHODS, AND COMPONENTS FOR TRANSFERRING MEDICAL FLUIDS

CROSS-REFERENCE TO RELATED APPLICATIONS

This application is a divisional of U.S. patent application Ser. No. 15/991,385, filed May 29, 2018, titled "SYSTEMS, METHODS, AND COMPONENTS FOR TRANSFERRING MEDICAL FLUIDS," which claims the benefit under 35 U.S.C. § 120 and 35 U.S.C. § 365(c) as a continuation of International Application No. PCT/US2016/064467, designating the United States, with an international filing date of Dec. 1, 2016, titled "SYSTEMS, METHODS, AND COMPONENTS FOR TRANSFERRING MEDICAL FLUIDS," which claims priority to U.S. Application No. 62/263,541, filed Dec. 4, 2015, titled "SYSTEMS, METHODS, AND COMPONENTS FOR TRANSFERRING MEDICAL FLUIDS" and claims priority to U.S. Application No. 62/360,900, filed Jul. 11, 2016, titled "SYSTEMS, METHODS, AND COMPONENTS FOR TRANSFERRING MEDICAL FLUIDS," the entire contents of each of which are incorporated by reference herein and made a part of this specification.

BACKGROUND

Field

This invention relates generally to medical fluid transfer systems, methods, and components; and specifically to electronically controlled medical fluid transfer systems, methods, and components.

Description of the Related Art

Many types of medical fluids are routinely used to treat patients, including chemotherapy drugs, antibiotics, immunosuppressive drugs, antiviral drugs, hydrating fluids, nourishing fluids, anticoagulants, pain management drugs, contrast fluids for medical imaging, etc. All of these fluids, in turn, come in many different varieties with advantages and disadvantages for various types of diseases, conditions, injuries, or therapies. Moreover, particular patients require optimized dosages, concentrations, and combinations of these drugs or other medical fluids to address their specific medical needs. As a result, medical facilities are required to provide many different types of customized medical fluids on a continual basis to meet individual patient needs.

SUMMARY

In some embodiments, a medical fluid transfer module is configured to be removably coupled to an electronic medical fluid transfer device to facilitate the transfer of medical fluids from a source container to a destination container. The medical fluid transfer module can comprise a first closeable, resealable medical connector and a second closeable, resealable medical connector, a multidirectional flow-control valve with a driving interface configured to interface with an electromechanical driver of an electronic medical fluid transfer device, and an intermediate container. The multidirectional flow-control valve can comprise a plurality of functional positions to enable a selection among a plurality of different fluid pathways within the medical fluid transfer module. The plurality of different fluid pathways can be configured to contain liquid within the medical fluid transfer module in a closed system when the medical fluid transfer module is not attached to the electronic medical fluid transfer device.

In some embodiments, a method of enabling medical fluid transfer between a source container and a destination container can comprise the steps of providing a closed-system fluid transfer module comprising a first closeable, resealable medical connector and a second closeable, resealable medical connector, a multidirectional fluid control valve with a driving interface configured to interface with an electromechanical driver of an electronic medical fluid transfer device, and an intermediate container or an intermediate pumping region; and instructing a user to couple the closed-system fluid transfer module to the electronic medical fluid transfer device.

In some embodiments, an electronic medical fluid transfer device can comprise one or more supports configured to receive a fluid transfer module comprising a first inlet fluid connector, a second outlet fluid connector, a multidirectional flow control valve, and an intermediate container or pumping region; a gas sensor configured to detect whether gas is present in the fluid transfer module; a first electromechanical driver configured to interface with and control the multidirectional flow control valve on the fluid transfer module; a second electromechanical driver configured to be mechanically linked to the intermediate container or pumping region; and a computer processor or processors configured to communicate electronically with the sensor and the first and second electromechanical drivers to prime or purge the fluid transfer module with liquid and purge gas from the fluid transfer module.

In some embodiments, the priming of the fluid transfer module can comprise the steps of opening a fluid pathway between the second fluid connector and the intermediate container or pumping region and closing a fluid pathway to the first fluid connector; lowering the pressure in the intermediate container or pumping region; opening a fluid pathway between the inlet fluid connector and the intermediate container or pumping region and closing the fluid pathway to the second fluid connector; pushing fluid from the intermediate container or pumping region toward the first fluid connector; opening the fluid pathway between the first fluid connector and the second fluid connector and closing the fluid pathway to the intermediate container or pumping region; and opening the fluid pathway between the first fluid connector and the intermediate container or pumping region.

BRIEF DESCRIPTION OF THE DRAWINGS

Embodiments will now be described with reference to the following drawings, which are provided by way of example, and not limitation. Like reference numerals indicate identical or functionally similar elements.

FIG. $2A_i$ is a front perspective view of an example of an electromechanical system for transferring medical fluid.

FIG. $2B_i$ is a rear view of an example of a fluid transfer device.

FIG. $2C_i$ is a front perspective view of the electromechanical system for transferring medical fluid of FIG. $2A_i$ with the fluid transfer device of FIG. $2B_i$ attached to it.

Figure 2A:
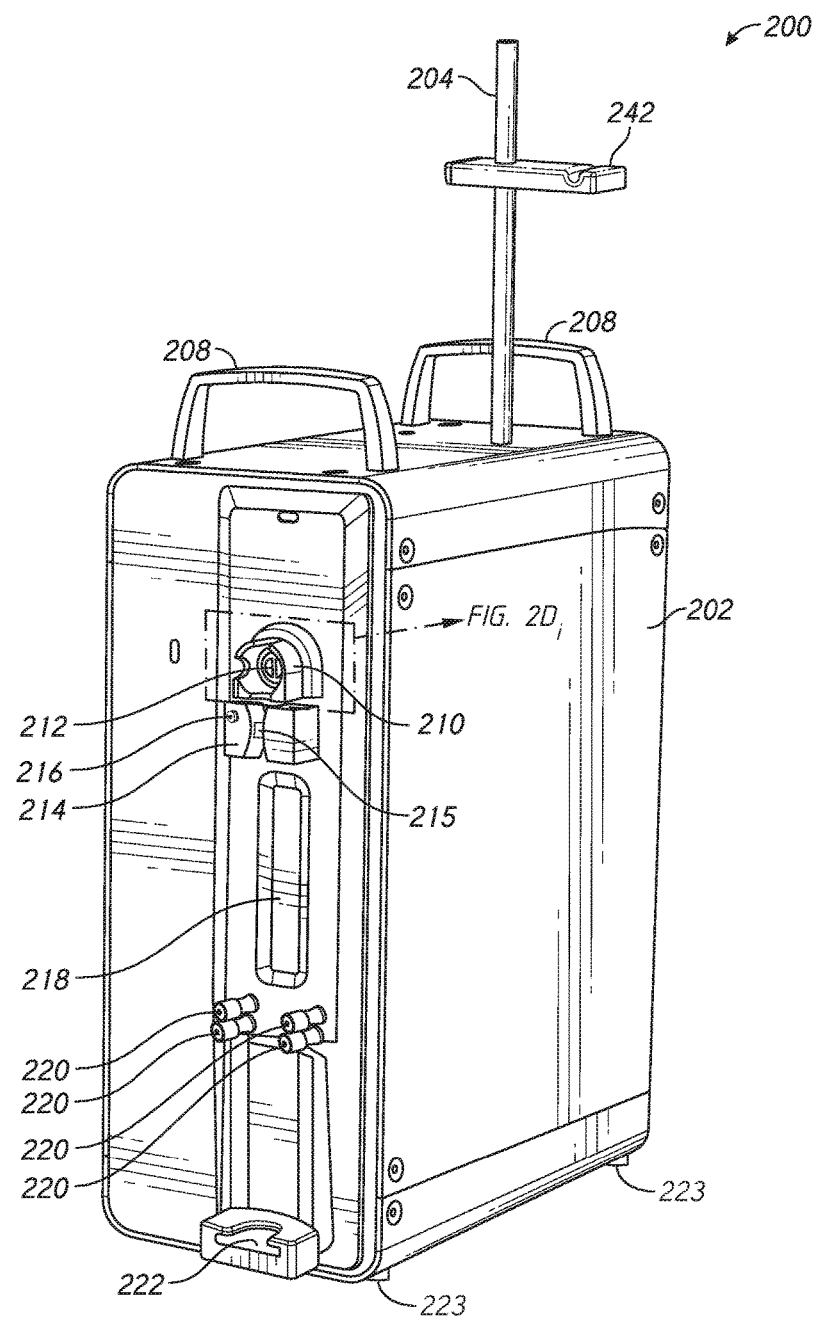
Figure 2B:
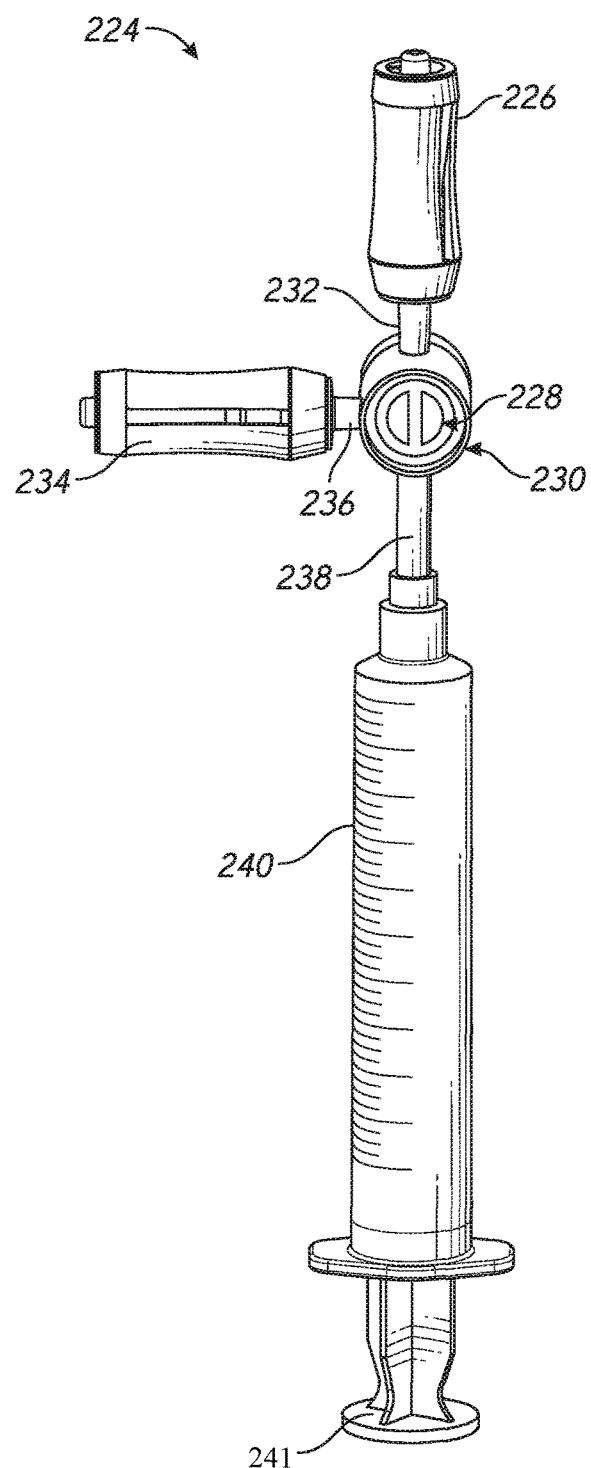
Figure 2C:
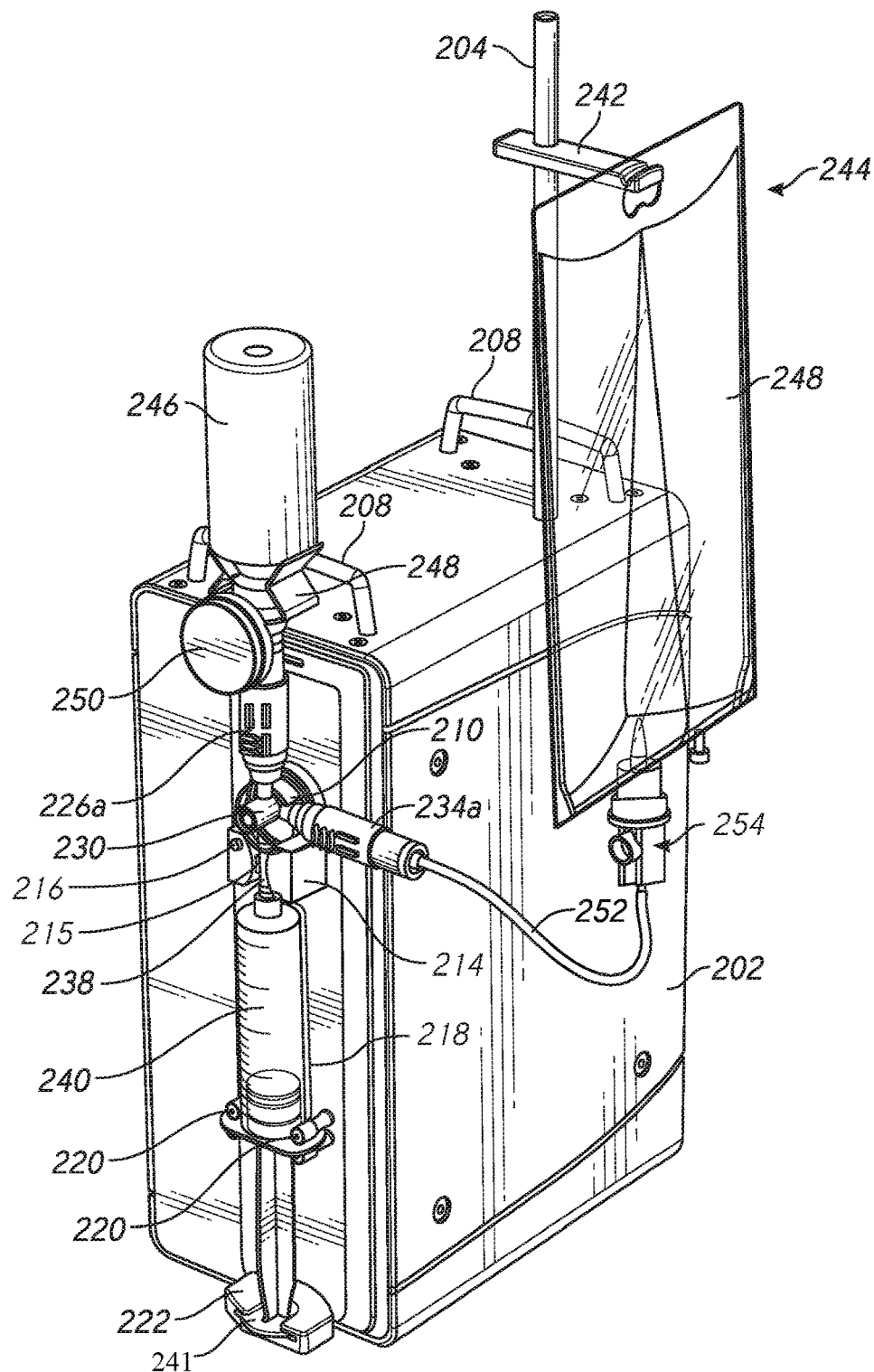
Figure 2D:
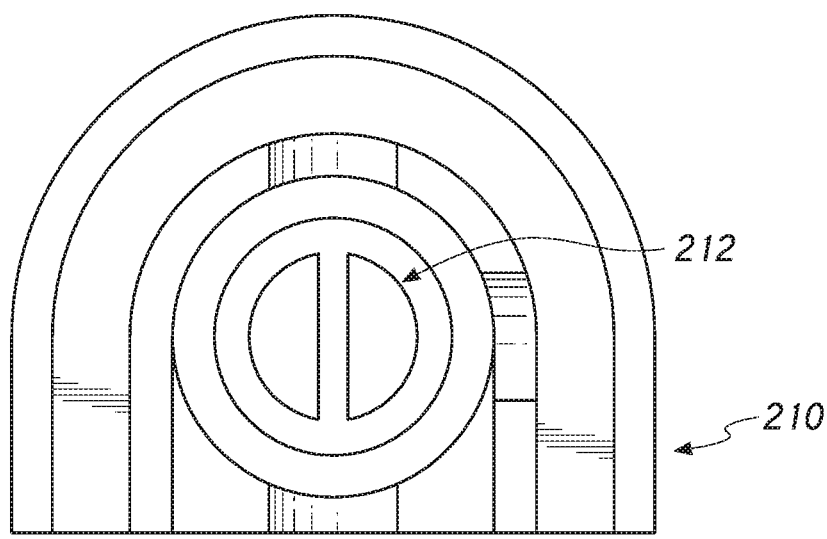

FIG. 2D$_i$ is a magnified partial front view of the electromechanical system of FIG. 2A$_i$ which illustrates an example of a driver.

FIG. 2A$_{ii}$ is a front perspective view of an example of an electromechanical system for transferring medical fluid according to another embodiment.

FIG. 2B$_{ii}$ is a rear view of an example of a fluid transfer device according to another embodiment.

FIG. 2C$_{ii}$ is a front perspective view of the electromechanical system for transferring medical fluid of FIG. 2A$_{ii}$ with the fluid transfer device of FIG. 2B$_{ii}$ attached to it.

FIG. 2D$_{ii}$ is a magnified partial front view of the electromechanical system of FIG. 2A$_{ii}$ which illustrates an example of a driver.

FIG. 2E$_{ii}$ is a rear perspective cross-sectional view of the electromechanical system and fluid transfer device shown FIG. 2C$_{ii}$.

Figure 3:
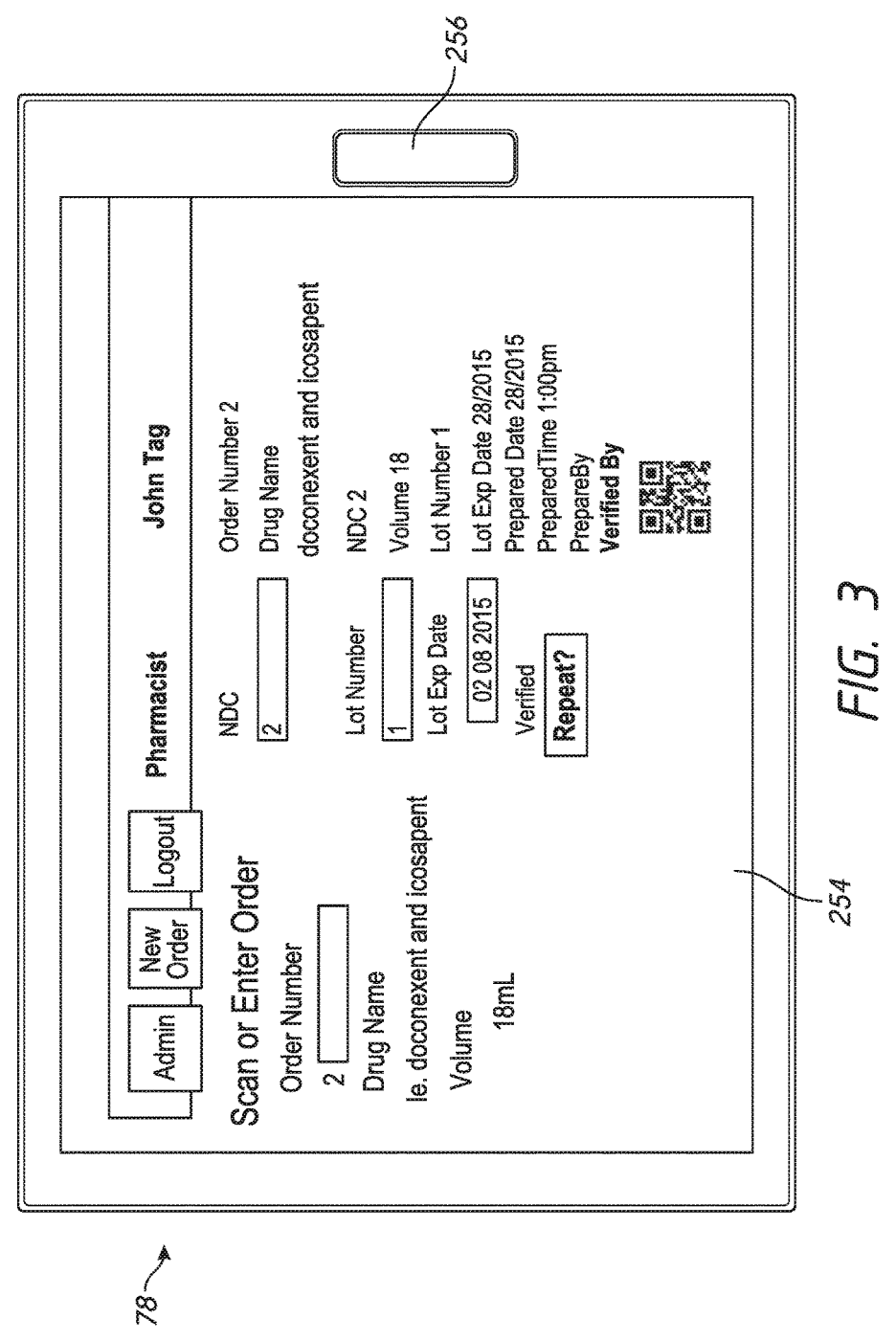

FIG. 3 is a front plan view of an example of a user control device.

Figure 4:
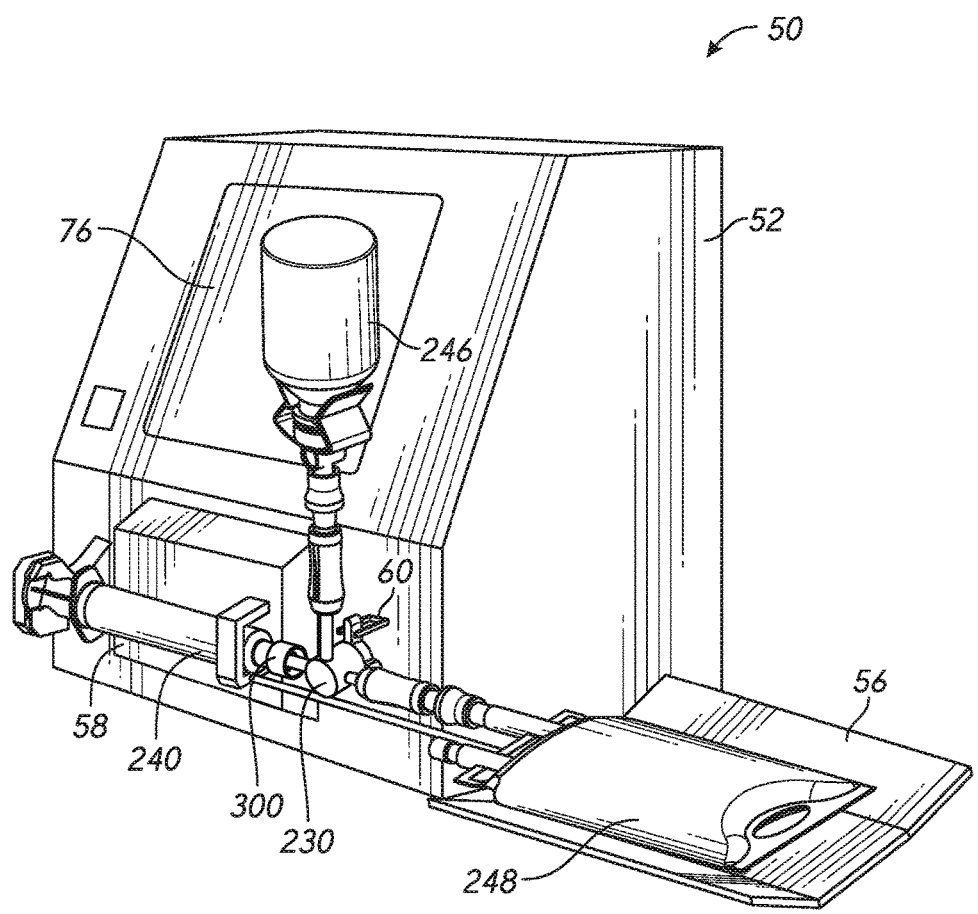

FIG. 4 is a front perspective view of another example of an electromechanical system for transferring medical fluid.

Figure 5:
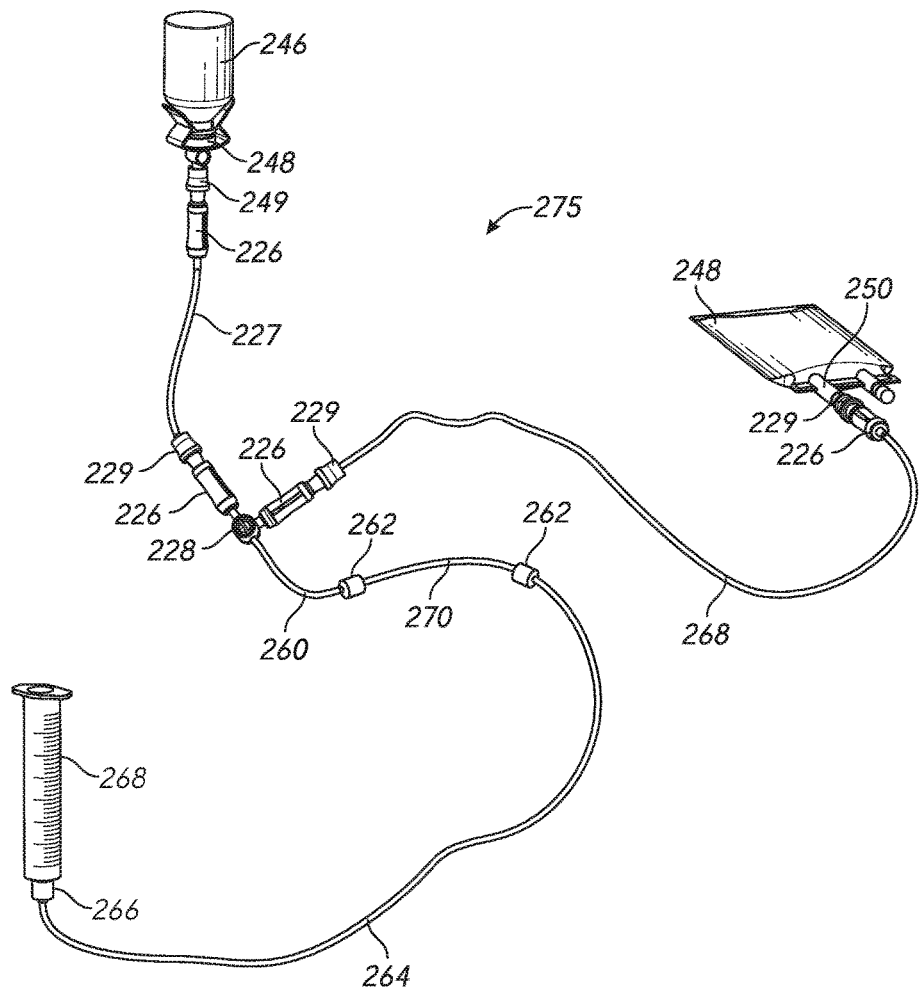

FIG. 5 is a perspective view of a fluid transfer device for use in an electromechanical system for transferring medical fluid.

FIG. 6 is a front plan view of another example of an electromechanical system for transferring medical fluid using the fluid transfer device of FIG. 5.

Figure 6A:
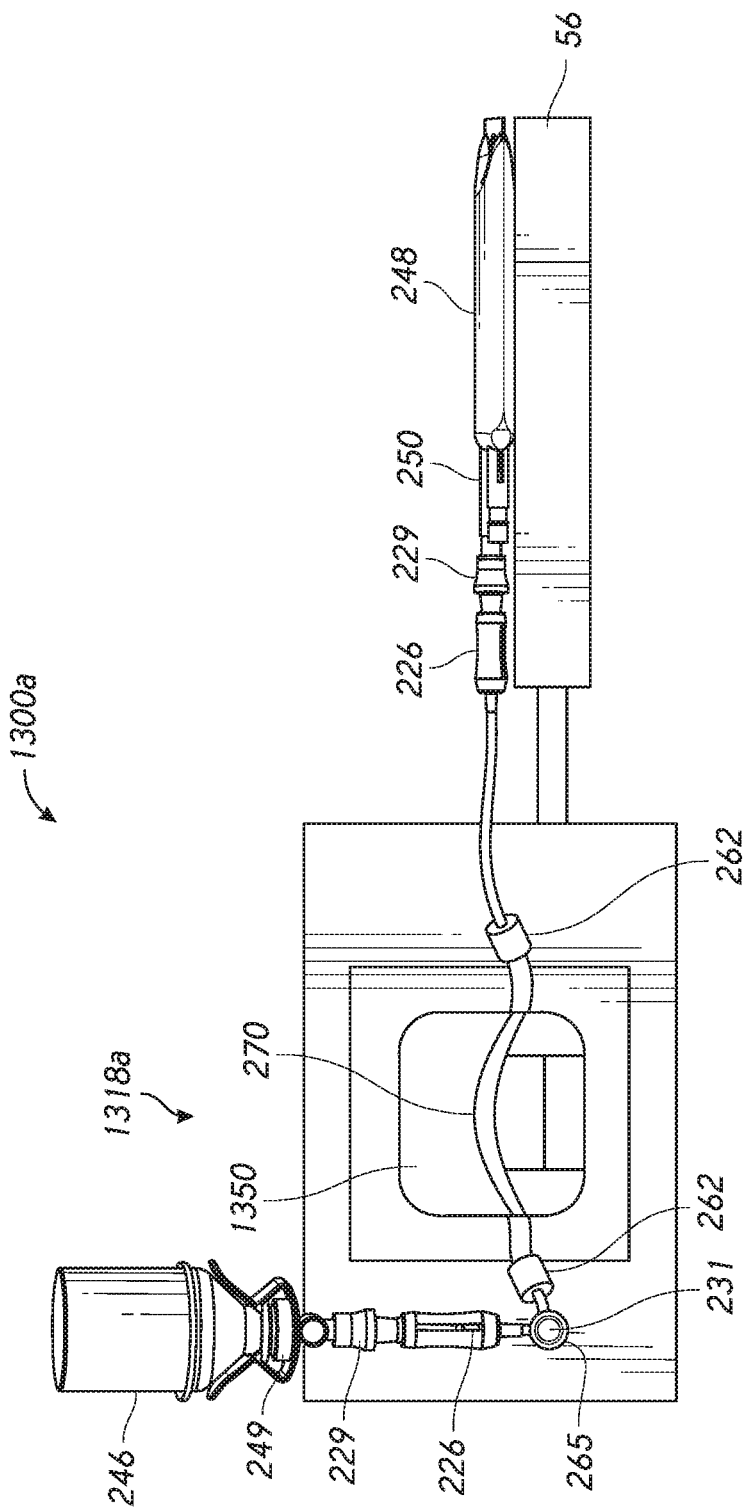

FIG. 6a is a front plan view of another example of an electromechanical system for transferring medical fluid using the fluid transfer device of FIG. 5.

Figure 7:
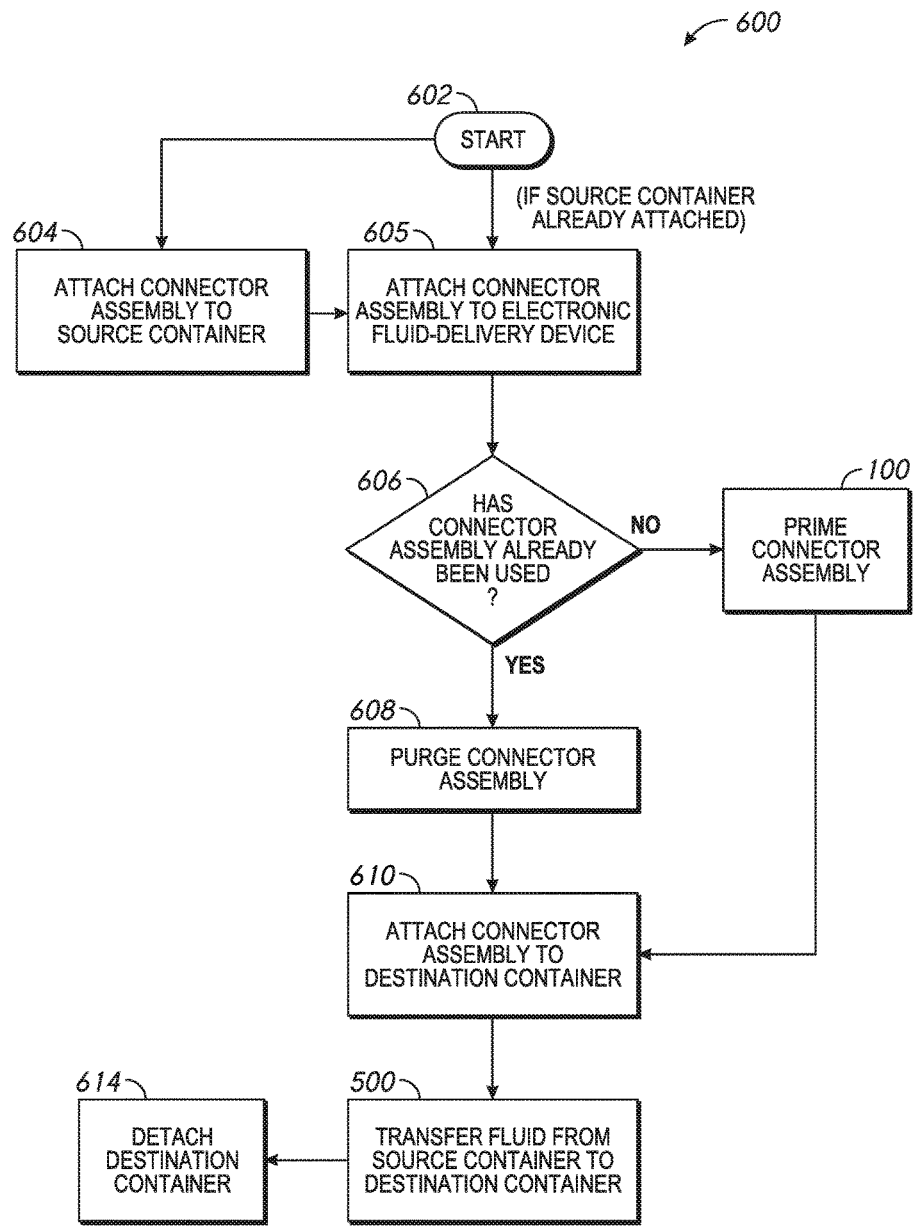

FIG. 7 is a flow chart illustrating an example of a fluid transfer method.

Figure 8A:
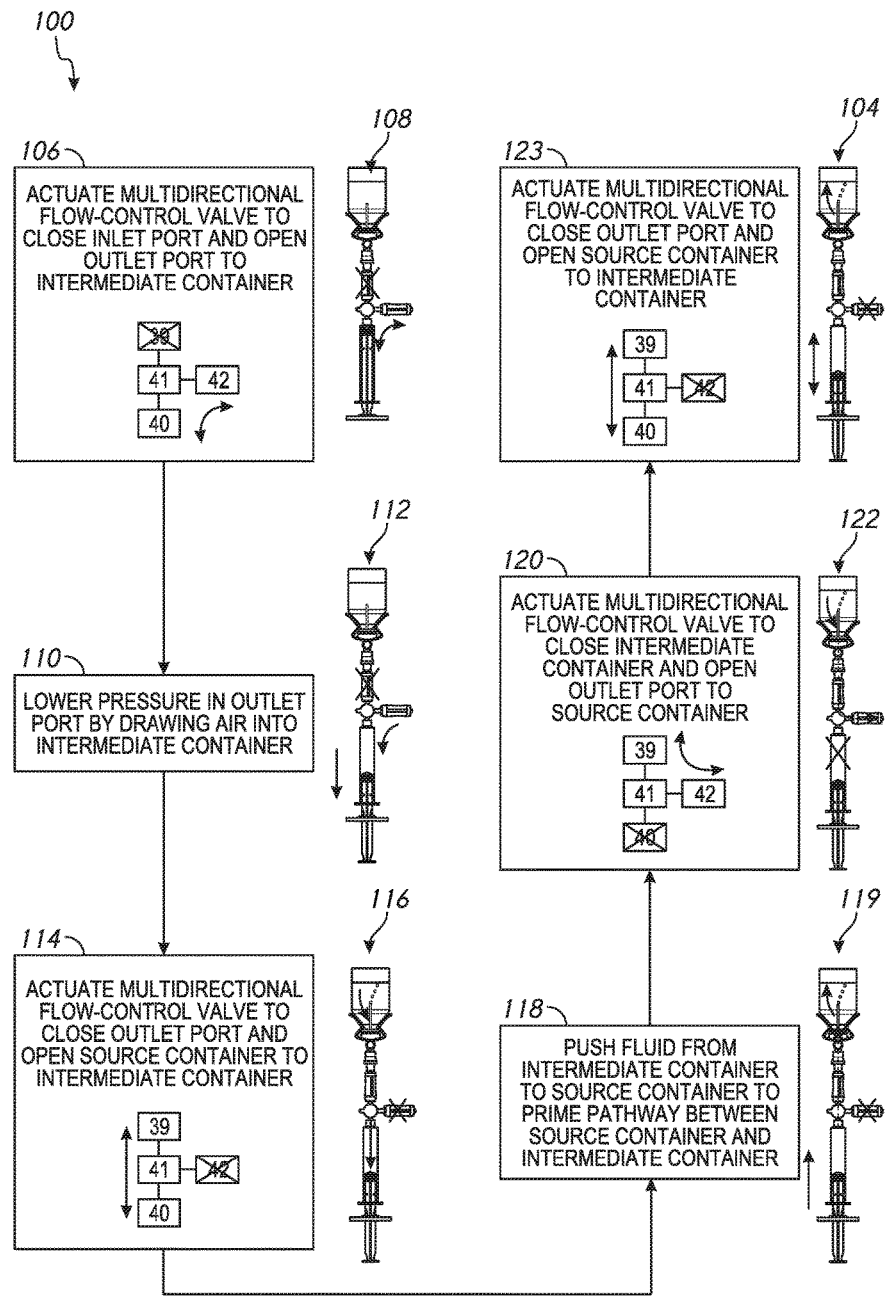

FIG. 8A is a flow chart illustrating an example of the priming step of the fluid transfer method of FIG. 7.

Figure 8B:
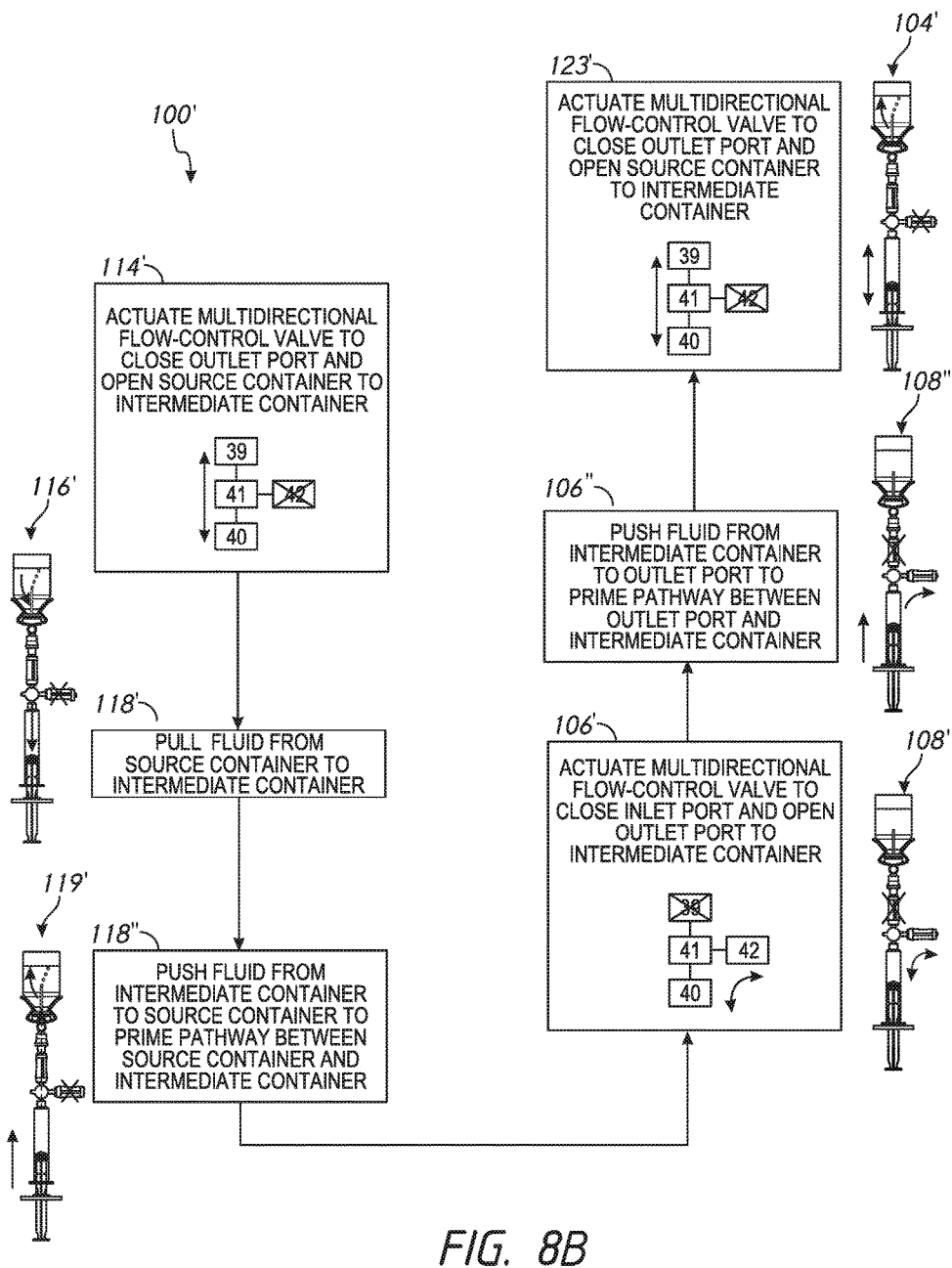

FIG. 8B is a flow chart illustrating an example of the priming step of the fluid transfer method of FIG. 7.

Figure 9:
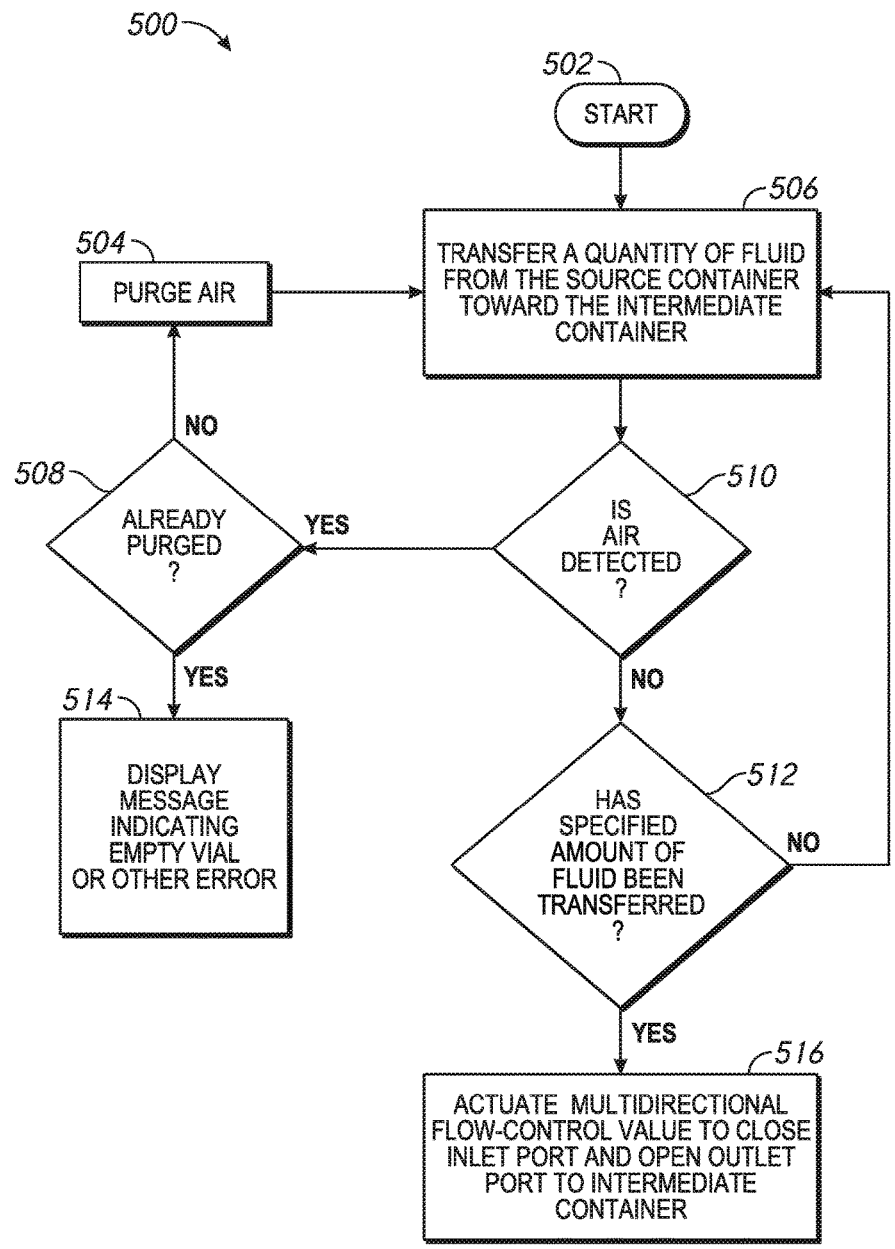

FIG. 9 is a flow chart illustrating an example of the fluid transfer step of the fluid transfer method of FIG. 7.

Figure 10:
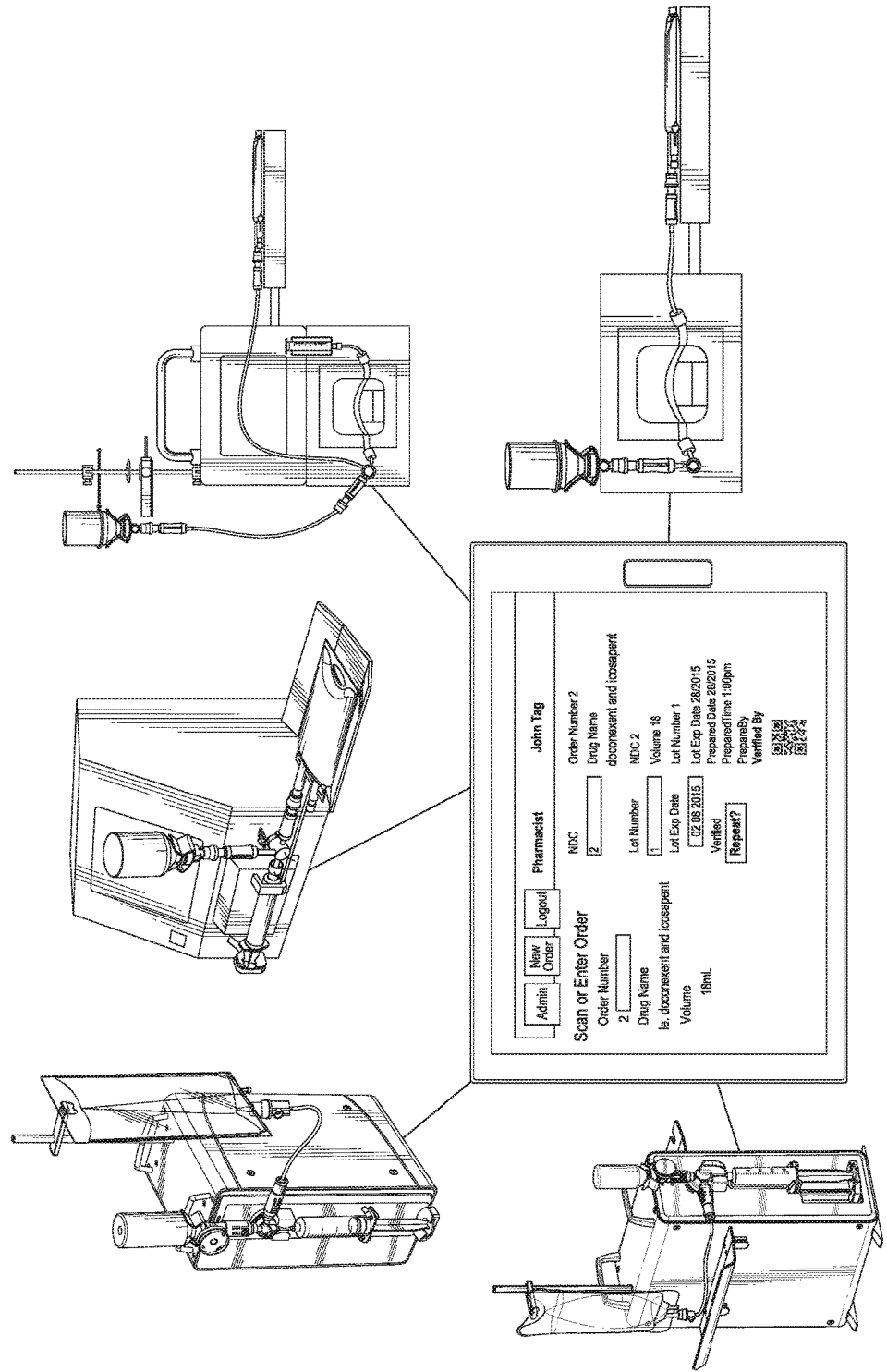

FIG. 10 is a schematic illustration of a user interface configured to electronically communicate with a plurality of different types of medical fluid transfer devices.

DETAILED DESCRIPTION

Various systems, methods, and components can be used in different embodiments of the inventions. Some embodiments are illustrated in the accompanying figures; however, the figures are provided for convenience of illustration only, and should not be interpreted to limit the inventions to the particular combinations of features shown. Rather, any feature, structure, material, step, or component of any embodiment described and/or illustrated in this specification can be used by itself, or with or instead of any other feature, structure, material, step, or component of any other embodiment described and/or illustrated in this specification. Nothing in this specification is essential or indispensable.

Figure 1A:
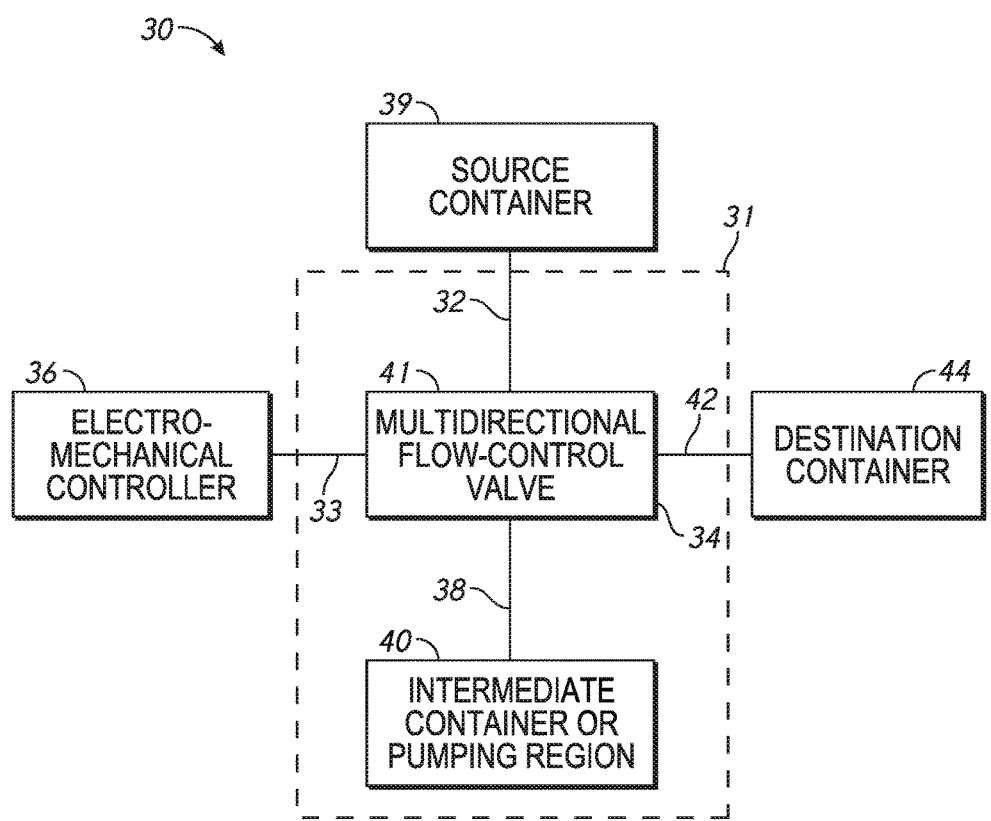
FIG. 1A is a schematic illustration of an example of a fluid transfer device removably attached to and/or in selective communication with other components of a fluid transfer system.

FIG. 1A is an example of a schematic illustration of a fluid transfer device 30 removably attached to and/or in selective communication with other components of a fluid transfer system. In some embodiments, a fluid transfer device 30 can comprise a source container 39, a fluid transfer module 31, an electromechanical controller 36, and a destination container 44. The source container 39 and the fluid destination container 44 can each comprise any suitable device for holding or supplying medical fluids, such as a vial, a bottle, a bag, a hose, a tube, a tank, a canister, etc. In some embodiments, the fluid destination container 44 is a type of container that is selected to be particularly well suited in size and structure for easy and convenient storage or transportation from a fluid transfer station to a patient treatment location, such as an intravenous fluid storage bag or IV bag, to provide an individual-patient, single-dosage supply of medical fluid. In some embodiments, the source container 39 is a type of container that is sufficiently large to provide multiple single-patient doses to be transferred into multiple destination containers 44 (either serially or in parallel). Some examples of fluid transfer devices 30 are illustrated and described in U.S. Pat. No. 8,522,832; U.S. Patent Application Publication No. 2014/0299221; PCT International Application No. US2015/040174; and U.S. Patent Application Publication No. 2015/0283322, all of which are incorporated by reference in their entireties and made a part of this specification, and any feature, structure, material, step, or component of any embodiment described and/or illustrated in any of these can be used with or instead of any other feature, structure, material, step, or component of any embodiment described and/or illustrated elsewhere in this specification.

The fluid transfer module 31 can comprise a multidirectional flow-control valve 41 and an intermediate container or pumping region 40, as well as any connector(s) and/or conduit(s) that may extend between or among these or any other components of the fluid transfer module 31, and/or any connectors and/or conduits that may extend between or among the fluid transfer module 31 and the source container 39 and/or the destination container 44. For example, the fluid transfer module 31 can comprise an inlet fluid connector 32 and tubing that can be configured to removably attach the multidirectional flow-control valve to the source container 39; and/or the fluid transfer module 31 can comprise an outlet fluid connector 42 and tubing that can be configured to removably attach the multidirectional flow control valve to the destination container 44.

As shown in FIG. 1A, the fluid transfer module 31 can comprise an intermediate fluid connector 38 that fluidly connects the multidirectional flow-control valve 41 and the intermediate container or pumping region 40. In some embodiments, the intermediate fluid connector 38 is a conduit and/or a tube attached by an appropriate permanent, fluid-tight method (e.g., adhesive, bonding, ultrasonic welding, etc.) between the multidirectional flow-control valve 41 and the intermediate container or pumping region 40. The intermediate container or pumping region 40 can comprise any suitable container or region that is configured to hold and measure fluids and/or to assist in providing an impetus for fluid-flow along a fluid conveying path. For example, in some embodiments, the intermediate container or pumping region 40 can be a syringe or a region of a conduit that is configured to interface with a peristaltic pump, or any other suitable intermediate device. Not all fluid transfer modules 31 will include all of the components or features illustrated or described in this specification; rather, one or more components or features can be omitted in any suitable embodiment.

The multidirectional flow-control valve 41 can be configured to mechanically attach to or interface with the electromechanical controller 36. For example, in some embodiments, the multidirectional flow-control valve 41 can comprise a driving interface 33 that is configured to attach with and/or interface with a corresponding electromechanical driver (see, e.g., FIGS. 2Ai, 2Di, 2Aii, 2Dii) of the electromechanical controller 36. The electromechanical controller 36 can actuate the multidirectional flow-control valve 41 under the control of one or more algorithms or instructions provided by a computer processor or a plurality of computer processors in the fluid transfer management system 74 (see FIG. 1B) that is or are configured to send one or more electronic signals to the electromechanical controller 36 to select among a plurality of functional positions on the multidirectional flow-control valve 41; however, any suitable computer processing arrangement capable of controlling the multidirectional flow-control valve 41 can be used and is envisioned and contemplated herein. Any disclosure in this specification of a single computer processor applies to and can be used with a plurality of computer processors.

In some embodiments, the multidirectional flow-control valve 41 can comprise a stopcock with a plurality of functional positions, such as a first position that enables fluid communication between the outlet fluid connector 42 and the intermediate container or pumping region 40 (but not the inlet fluid connector 32, in some embodiments); a second position that enables fluid communication between the inlet fluid connector 32 and the intermediate container or pumping region 40 (but not the outlet fluid connector 42, in some embodiments); and a third position that enables fluid communication between the outlet fluid connector 42 and the inlet fluid connector 32 (but not the intermediate container or pumping region 40, in some embodiments). For example, in some embodiments, when the stopcock is in the first position, fluid can flow from the intermediate container or pumping region 40 to the destination container 44 or vice versa; when the stopcock is in the second position, fluid can flow from the source container 39 to the intermediate container or pumping region 40 or vice versa; and when the stopcock is in the third position, fluid can flow from the source container 39 to the destination container 44 or vice versa. Further, in some embodiments, when the stopcock is in the first position, the intermediate fluid connector 38, the stopcock, and the outlet fluid connector 42 can comprise at least a portion of a flow path between the intermediate container or pumping region 40 and the destination container 44; when the stopcock is in the second or fourth position, the inlet fluid connector 32, the stopcock, and the intermediate fluid connector 38 can comprise at least a portion of a flow path between the source container 39 and the intermediate container or pumping region 40; and when the stopcock is in the third position, the inlet fluid connector 32, the stopcock, and the outlet fluid connector 42 can comprise at least a portion of a flow path between the source container 39 and the destination container 44. In some embodiments, the stopcock can comprise at least a portion of one or more flow paths between or among two or more containers (e.g., the source container 39, the intermediate container or pumping region 40, and/or the destination container 44) without the use of any connectors (e.g., the inlet fluid connector 32, the intermediate fluid connector 38, and/or the outlet fluid connector 42) when in the first, second, third, and/or fourth position. Other arrangements can be used are also appreciated and contemplated herein, including, for example, stopcocks configured to have more or less than three positions (e.g., stopcocks configured to have 2, 4, 5, or more positions).

In some embodiments, the fluid transfer module 31 can be a single-use or limited-use, disposable device that is configured to be periodically removed from and replaced within the fluid transfer device 30, such as after a single dosage of medication for a particular patient has been transferred and/or after one particular type of medication has passed through the fluid transfer module 31 (e.g., to avoid mixing of medications when not desired).

Figure 1B:
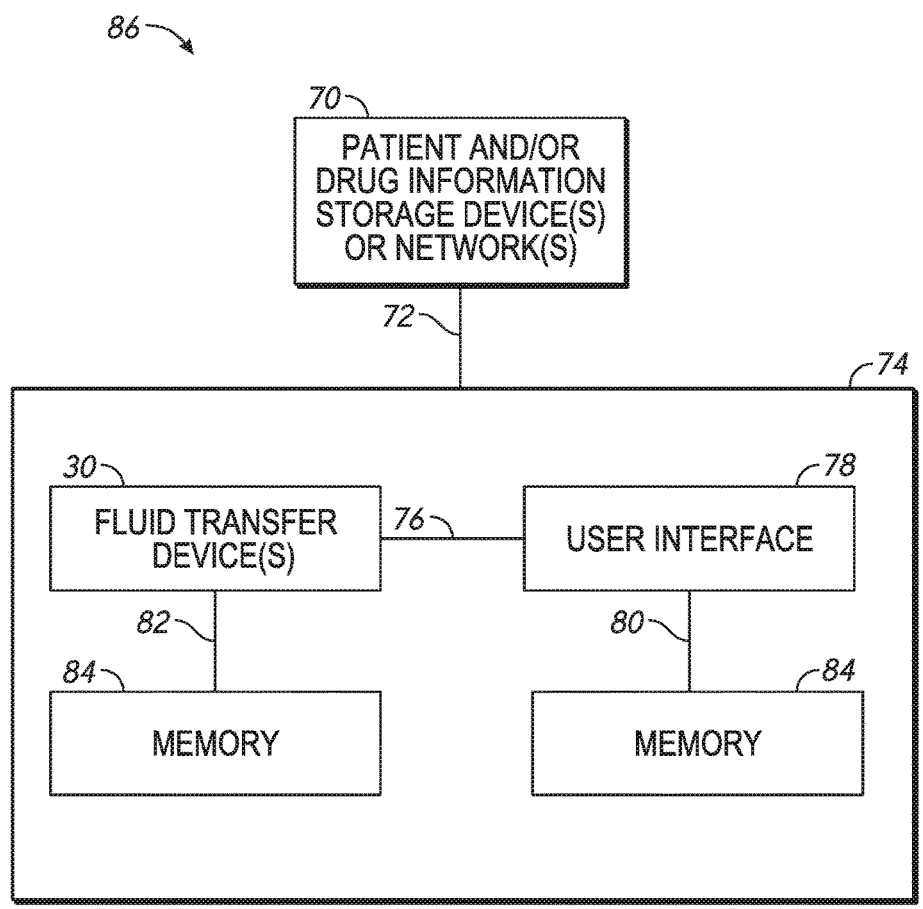
FIG. 1B is a schematic illustration of an example of a system for transferring medical fluid that includes the fluid transfer device of FIG. 1A.

FIG. 1B is a schematic illustration of a fluid transfer system 86 for transferring medical fluid that includes the fluid transfer device 30 of FIG. 1A, according to some embodiments. For example, as shown in FIG. 1B, one or more fluid transfer devices 30 can form part of a fluid transfer system 86 that can include one or more of the following components that can be selectively positioned in electronic communication between or among each other: one or more electronic patient and/or drug information storage devices or networks 70; one or more fluid transfer management systems 74 comprising one or more fluid transfer devices 30, a user interface 78, and/or one or more memories 84. In some embodiments, the one or more electronic patient and/or drug information storage devices or networks 70 can be physically remote from the fluid transfer management system 74. For example, in a health clinic or hospital, the one or more electronic patient and/or drug information storage devices or networks 70 can comprise a remote patient information management system with a database that can be queried to provide information about a particular patient's needs for medical fluids (e.g., a drug prescription) that may include the type, dosage, lot number, expiration date, and/or concentration of one or more drugs or other medical fluids to be provided to a patient, and/or identifying information regarding one or more health care provider who prescribed, requested, and/or filled the destination container, and/or the time and/or date associated with any or all of these activities. Any medical information, such as any of the foregoing medical information, can be provided by the one or more fluid transfer devices 30 for recording and storage in the patient information management system.

The various components of the fluid transfer system 86 can communicate between or among themselves in any suitable manner. For example, as illustrated, the one or more patient and/or drug information storage device(s) or network(s) 70 can electronically communicate with the fluid transfer management system 74, or any components thereof, by way of an electronic communication link 72, formed by any suitable electronic communication device, such as a wired connection, a local area network, a wide area network, the Internet, and/or a wireless connection (including, e.g., Wi-Fi, Bluetooth, Ant+, ZigBee, cellular, etc.), or any other electronic communication device (collectively referred to as "electronic communicators"). As shown in FIG. $2E_{ii}$, the fluid transfer management system 74 may comprise a wireless communication console 299, such as a Wi-Fi box that is configured to send and/or receive data, including patient data, data regarding a fluid transfer, data regarding the type, dosage, concentration, volume, image, technician, physician, and/or time of a fluid transfer, and/or data to control the electronic fluid transfer system 86, etc. The fluid transfer device 30 can communicate with a memory 84 by any suitable electronic connection, such as a wired connection, or any other electronic communicators. In some embodiments, the memory 84 is part of the fluid transfer device 30, in that a common housing is provided for containing or supporting both.

The user interface 78 can communicate with one or more fluid transfer devices 30 and/or with one or more patient and/or drug information storage device(s) or network(s) 70 by way of any suitable electronic communication device 76, including by way of any wireless device or by way of any other of the electronic communicators. In some embodiments of the fluid transfer management system 74 in which there are multiple fluid transfer devices 30, a single user interface 78 can electronically communicate with a plurality of fluid transfer devices 30 to control and/or monitor multiple fluid transfers operating generally simultaneously or generally in parallel. In some embodiments of the fluid transfer management system 74 in which there are multiple fluid transfer devices 30, one or more user interfaces 78 can electronically communicate with a plurality of fluid transfer devices 30 to control and/or monitor multiple fluid transfers operating generally simultaneously or generally in parallel. The user interface 78, like the fluid transfer device 30, can electronically communicate with or include a memory 84 by way of a wired connector 80 or any other of the electronic communicators. The memory 84 of the user interface 78 can be part of the user interface 78 in that a common housing can be provided for containing or supporting both. Each of the components of the fluid transfer management system 74 as shown in FIG. 1B (e.g., the fluid transfer device(s) 76, the user interface 78, and the memory or memories 84) can be provided in a single housing, or can be provided as discrete components or discrete collections of components.

FIGS. $2A_i$-$2D_i$ illustrate various features, components, and arrangements that can be included in some embodiments of the fluid transfer device 30 and fluid transfer module 31 shown in FIG. 1A and the fluid transfer management system 74 shown in FIG. 1B. As will be described in more detail below, FIG. $2A_i$ illustrates an example of an electromechanical system 200 (also referred to as a fluid transfer unit 200); FIG. $2B_i$ illustrates an example of a fluid transfer module 31 in the form in this example of a fluid pump assembly 224; FIG. $2C_i$ illustrates the fluid pump assembly 224 of FIG. $2B_i$ removably attached to the fluid transfer unit 200 of FIG. $2A_i$; and FIG. $2D_i$ illustrates an example of a portion of an electro-mechanical controller 36 in the form in this example of a driver 212. Unless otherwise noted, like reference numerals among FIGS. $2A_i$-$2D_i$ indicate identical or functionally and/or structurally similar elements, and reference numerals in the below discussion corresponding to elements labeled in FIGS. 1A and 1B refer to elements that are the same as or generally similar to the elements of FIGS. 1A and 1B.

Turning to FIG. $2A_i$ this figure illustrates an example of a portion of a fluid transfer management system 74 with a remote user interface 78, as identified in FIG. 1B. For example, in some embodiments, FIG. $2A_i$ illustrates a front perspective view of a fluid transfer unit 200 for transferring medical fluid. In some embodiments, the fluid transfer unit 200 is an example of a portion of the fluid transfer device 30 shown in FIG. 1A or the fluid transfer system 86 shown in FIG. 1B. As shown in the figures, the fluid transfer management system 74 can comprise a fluid transfer unit 200 that comprises a housing 202, one or more carrying handles 208, one or more base supports 223, a destination-container support (e.g., a generally vertical pole stand 204 and/or a generally horizontal support arm 242), and one or more supports configured to receive and retain at least a portion of the fluid transfer module 31 (e.g., the intermediate container or pumping region 40). In some embodiments, the supports can include one or more protruding holders 220, one or more receptacles 218 (such as a recess 218, as illustrated); one or more sensor devices 214 with one or more channels that include one or more sensors 215; one or more movable platforms 222 for receiving at least a portion of the fluid transfer module 31 and/or for facilitating the transfer of fluid; and/or one or more attachment regions 210 for attaching to or receiving a multidirectional flow-control valve 41. As will be described in more detail below, the fluid transfer device 30 or the fluid transfer unit 200 can include a driver 212, which can form part of the electro-mechanical controller 36 of FIG. 1A, and the one or more sensor devices 214 can include one or more indicators 216. The one or more base supports 223 can be attached to or integrally formed with the housing 202 to help stabilize the fluid transfer unit 200 (e.g., to help prevent it from tipping over). Although not shown in FIG. $2A_i$, in some embodiments, the one or more base supports 223 can extend across an underside of the housing 202.

In some embodiments, at least one or more portions of the housing 202, such as the one or more receptacles 218 (e.g., the recess 218 illustrated in FIG. $2A_i$), can be transparent to enable one or more measuring instruments positioned inside of the housing 202 to capture an image or other data on the outside of the housing. For example, a volume sensor (see FIG. 2Eii) can determine the volume of liquid being transferred to one or more containers (e.g., source container 39, intermediate container or pumping region 40, and/or destination container 44). For example, in some embodiments, the volume sensor can be configured to sense the volume in the intermediate container or pumping region 40 through the transparent recess 218. It will be understood that this same volume sensor or one or more other volume sensors can be configured to sense the volume of one or more other containers in addition to or in lieu of the intermediate container or pumping region 40 (e.g., the source container 39 and/or the destination container 44, among others), for example, through one or more transparent receptacles 218 and/or through one or more other sections of the housing 202 that are transparent. The volume sensor can comprise, for example, any appropriate sensor or combination of sensors to provide information about the volume of the liquid in a container, such as an optical sensor (e.g., a camera or a break-beam sensor), an infrared sensor, an acoustic sensor (e.g., an ultrasonic sensor), and/or a mass or weight sensor, among others.

The volume sensor can be used, for example, to control and/or to provide a record of the volume and/or type of fluid transferred to a patient, such as, for example, by sensing and/or recording the volume and/or one or more other characteristics (e.g., color, viscosity, concentration, lot number, expiration date, etc.) of the liquid in a container (e.g., the intermediate container, or pumping region 40, and/or the source container 39 and/or the destination container 44) before, during, and/or after it is transferred to a patient. For example, in some embodiments, a camera can be used to capture an image of the intermediate container or pumping region 40 to confirm or measure the volume therein. A data file can then be created and stored in a memory 84 which has one of more items of information, such as patient identifying information, the date and time the liquid was transferred and/or the volume or other characteristic(s) of the liquid was or were confirmed and recorded, the type (name, brand, and/or concentration, etc.) of medical fluid transferred, the volume of medical fluid transferred, and/or one or more images of the intermediate container or pumping region 40 with liquid inside, etc. The same or a similar data file can be created for any one of the suitable volume sensors described above. In some embodiments, the fluid transfer unit 200, the fluid transfer device 30, and/or the fluid transfer system 86 can include one or more measuring instruments, such as one or more volume sensors. In some embodiments, the one or more measuring instruments or volume sensors can be internal and/or external to the fluid transfer unit 220, or partially external and partially internal, such as when a portion of the instrument or sensor is inside of the housing 212 and a portion of the sensor protrudes from the housing 212.

FIG. 2B$_i$ illustrates a rear view of an example of a fluid transfer module 31 of FIG. 1A in the form in this example of a fluid pump assembly 224, such as a multi-stroke fluid pump assembly 224. As shown in the figures, in some embodiments, the fluid pump assembly 224 comprises: an inlet fluid connector 32 in the form in this example of a conduit 232 and a selectively openable and closeable fluid connector 226; a multidirectional flow-control valve 41 in the form in this example of a fluid stopcock 230; an outlet fluid connector 42 in the form in this example of a conduit 236 and a selectively openable and closeable fluid connector 234; and an intermediate container 40 in the form in this example of a syringe pump 240 that is attached (e.g., bonded) to the fluid stopcock 230 via a conduit 238. The fluid pump assembly 224 can be a limited-use or single-use, disposable device that is configured to be routinely removed, discarded, and replaced with a new disposable device in position on the fluid transfer unit 200.

A multidirectional flow-control valve 41, such as a fluid stopcock 230, can be particularly useful in some embodiments because it can permit variability and control of the direction and/or orientation of the fluid pathway within the fluid transfer module 31. In some embodiments, the flow-control valve 41 can be configured, as illustrated throughout this specification, to selectively enable a plurality of discrete settings, each setting enabling fluid connections within the fluid pathway of the fluid transfer module 31 among two or more different components of the fluid transfer module 31, and closing-off or isolating one or more other fluid connections of one or more other components from the fluid pathway of the fluid transfer module 31. The flow-control valve 41 can be configured to change between the plurality of discrete settings.

In some embodiments, as illustrated, such change or changes of settings or connections within the flow-control valve 41 can be accomplished electronically and independently of changes to fluid pressure within the fluid transfer module 31. For example, in some embodiments, a pressure differential can arise between two or more parts or components of the fluid transfer module 31 without causing any change of connections within the fluid transfer module 31 and/or without enabling fluid communication between different portions of the fluid transfer module 31 that, before such pressure differential, were not previously in fluid communication with each other.

In some embodiments, the multidirectional flow-control valve 41 is not a one-way valve or a series of one-way valves; rather, the multidirectional flow-control valve 41, in each particular electronically selectable setting, can provide a full two-way fluid pathway between two or more components of the fluid transfer module 31. For example, in some embodiments, in one or a plurality of discrete, electronically selectable settings, the flow-control valve 41 can provide a two-way fluid pathway between the inlet fluid connector 226 and the outlet fluid connector 234; and/or a two-way fluid pathway between the inlet fluid connector 226 and the intermediate container 40 or syringe pump 240; and/or a two-way fluid pathway between the intermediate container 40 or syringe pump 240 and the outlet fluid connector 234. In some embodiments, the multidirectional flow-control valve 41 can enable fluid withdrawn from a source container 39 to be partially or fully returned to a source container 39, in some situations, which can be particularly advantageous, such as, for example, during priming and/or purging of a fluid transfer module 31, although other situations in which this type of fluid flow are also contemplated and can be used.

In some embodiments, either or both of the fluid connectors 226, 234 can be industry standard medical connectors (e.g., luer connectors complaint with ISO 594 or compliant with any other industry standard) that are resealable and fluid-tight, such as the Clave® female medical connector or the Spiros® male medical connector or either of the male or female sides of a Chemolock® medical connector system, all sold by ICU Medical, Inc. Examples of embodiments of these and other devices, among many others, that can be used as fluid connectors 226, 234, or as any portions thereof, are included in U.S. Pat. No. 5,873,862; 7,998,134; and U.S. Published Patent Application No. 2014/0246616, all of which are incorporate by reference in this specification in their entireties. Any feature, structure, material, step, or component described and/or illustrated in any of the foregoing patents or published application can be used with or instead of any feature, structure, material, step, or component described and/or illustrated in any other portion of this specification.

In some embodiments, the fluid stopcock 230 can comprise a device that selectively permits fluid communication between and/or among multiple apertures and/or channels in the stopcock 230. For example, as shown in FIG. 2B$_i$ and as described above, the fluid stopcock 230 can selectively permit fluid communication between any two of the inlet fluid connector 226, the outlet fluid connector 234, and the intermediate container 40 or syringe pump 240. The selection between and/or among the multiple apertures and/or channels in the stopcock 230 can be accomplished by actuating the stopcock 230, such as by utilizing an electromechanical controller 36 in the fluid transfer unit 200 to actuate a driving interface 33 on the stopcock 230, such as in the form in this example of a rotatable actuator 228. As described above, the electromechanical controller 36 can be controlled by sending one electronic signal or a series of electronic signals from one or more computer processors associated with the fluid transfer device 30. As shown in FIG. 2B$_i$ the rotatable actuator 228 can include one or more recesses and/or protrusions that are configured to interface with a driver 212 of a fluid transfer unit, such as a driver 212 that includes one or more recesses and/or protrusions that comprise one or more shapes that are complementary with or generally match or correspond with the recesses and/or protrusions of the actuator 228. As shown in FIG. 2E$_{ii}$, the driver 212 may be controlled via a driver motor 290 and driver shaft 292. The electromechanical controller 36 may send a signal activating driver motor 290 and driver shaft 292 to initiate driver 212 movement, and/or to continue and/or stop driver 212 movement. When a rotatable actuator 288 interfaces with the driver 212, the driver 212 may allow the electromechanical controller to select between and/or among the multiple apertures and/or channels in the stopcock 230. As in every embodiment in this specification, any component, structure, feature, or step that is illustrated and/or described in connection with FIG. 2Eii (including the internal components) can be used with or instead of any component, structure, feature, or step that is illustrated and/or described in connection with any other figure or embodiment in this specification.

FIG. 2D$_i$ is a magnified partial front view of the fluid transfer unit 200 of FIG. 2A$_i$, which illustrates an attachment region 210 and the recesses and/or protrusions of the driver 212, according to some embodiments. However, it will be understood that many different types and/or patterns of recesses and/or protrusions can be used, depending, for example, upon functional and aesthetic preferences. In some embodiments, one or more of the types and/or patterns of recesses and/or protrusions, and/or one or more of the types of materials (such as a tacky or slide-resistant material with a high coefficient of friction) can provide resistance to rotational disengagement or slipping during actuation.

Returning to FIG. 2B$_i$, this figure also illustrates an example of a syringe pump 240. In some embodiments, the syringe pump 240 includes an actuator, such as an actuating stem 241, that can be reciprocated back-and-forth or up-and-down to move an internal plunger, thereby decreasing or increasing the fluid-carrying volume inside of the syringe pump 240. A first stroke of the multi-stroke fluid pump assembly 224 in the form in this example of a syringe pump 240 can be accomplished by drawing the actuating stem 241 at least partially out of the body of the syringe pump 240, thereby drawing fluid into the syringe pump 240, and then reversing the direction of the syringe pump 240, pushing the actuating stem 241 back toward the body of the syringe pump 240, thereby expelling the drawn-in fluid out of the syringe pump 240.

In some embodiments, as shown, for example, in FIG. 2B$_i$, the conduit 238 of the multi-stroke pump assembly 224 can be longer than the conduits 232, 236 extending between the fluid stopcock 230 and the fluid connectors 226, 235. The conduit 238 can be permanently coupled to the fluid stopcock 230 on one end, and to the syringe pump 240 on the other end. Other arrangements are also contemplated and can be used.

As illustrated, in some embodiments, the fluid transfer module 31 (such as the fluid pump assembly 224) can form part of or constitute a closed system, in that: (i) liquid, or fluid, and/or vapors contained or sealed within the fluid transfer module 31 are prevented from exiting or escaping from the fluid transfer module 31, and/or (ii) the exiting or escaping of liquid, or fluid, and/or vapors is resisted in a clinically significant manner to diminish or avoid one or more clinical risks or negative outcomes, when the fluid transfer module 31 is disconnected from other components of the fluid transfer device 30. As shown, in some embodiments, the entire fluid pathway within the fluid transfer device 30 can constitute a closed system or a seal system. As used in this specification, the term "closed system" or "sealed" or any similar terms are used in accordance with their customary meanings in the field of medical infusion, and these terms include the requirement that fluids stay inside of the fluid transfer module 31 or the fluid transfer device 30 (or components thereof) under normal conditions or use such that any small amount of escaping fluid or vapors would not have any significant adverse clinical effects under normal conditions or use. In some embodiments, as shown in FIGS. 1A and 2B$_i$, the fluid transfer module 31 can be automatically closeable and resealable at each terminal end of the module 31 (e.g., at the inlet fluid connector 32, at the intermediate fluid connector 38, and/or at the outlet fluid connector 42). When either or both of the fluid transfer module 31 and/or the fluid transfer device 30 are sealed and/or constitute part of a closed system, the risk of ingress of harmful substances (e.g., bacteria or viruses or other microbes) into the fluid pathway is diminished, and the risk of egress of harmful substances (e.g., chemotherapy or immunosuppressive drugs) from the fluid transfer device 30 or the fluid transfer module 31 into the surrounding environment of a healthcare facility is diminished.

FIG. 2C$_i$ is a front perspective view of another type of fluid transfer module 31 that is removably attached to the fluid transfer unit 200 of FIG. 2Ai. The fluid transfer module 31 is identical to the fluid pump assembly 224 of FIG. 2B$_i$, except that Chemolock connectors 234a, 226a are used rather than Spiros connectors, in this example. Any suitable type of connector or combination of connectors can be used. As illustrated in FIG. 2C$_i$, the fluid transfer module 31 (also referred to as a multi-stroke fluid pump assembly 224) can be removably attached to the fluid transfer unit 200, such as by using one or more of the supports on the fluid transfer unit 200. For example, as shown in FIG. 2C$_i$, a flat portion or end of the actuating stem 241 can be inserted into or coupled with a receiving region of the movable platform 222; one or more tabs on the syringe pump 240 can be positioned on or inserted between one or more of the protruding holders 220; the body of the syringe pump 240 can be received in the receptacle 218; the conduit 238 can be inserted into or on the sensor device 214, such as in a channel within the sensor device 214 that includes one or more sensors 215 (also referred to as one or more sensing regions 215; and/or the body of the fluid stopcock 230 can be positioned in or on or inserted into the attachment region 210 of the fluid transfer unit 200. In some embodiments, the fluid transfer device 30, such as in the form in this example of a multi-stroke fluid pump assembly 224, can be attached to the fluid transfer unit 200 in a single motion by simply advancing the transfer device 30 into contact with a face on the fluid transfer unit 200 that includes one or more of the supports 220. The fluid transfer device 30 can be removably retained on the fluid transfer unit 200 by any suitable attachment structure, including a snap-fit, a friction fit, a clasp, a clip, a retaining arm or door, an elastic band, or any other attachment structure.

When the fluid transfer module 31 (e.g., the fluid pump assembly 224) is removably attached to the fluid transfer unit 200, a fluid-observation region on the conduit 238 of the fluid transfer device 30 can be positioned adjacent to or within an appropriate sensing distance from the one or more sensors 215. In the illustrated example, the fluid-observation region of the fluid transfer device 30 is at least a portion of the conduit 238 positioned between the multidirectional flow-control valve 41 (e.g., the fluid stopcock 230) and/or the intermediate container or pumping region 40 (e.g., the syringe pump 240). In some embodiments, the fluid-observation region of the fluid transfer device 30 can comprise a portion of the conduit 238 positioned between the multidirectional flow-control valve 41 (e.g., the fluid stopcock 230) and/or the intermediate container or pumping region 40 (e.g., the syringe pump 240). In some embodiments, the fluid-observation region can be positioned in another position on the fluid transfer device 30, or there can be multiple fluid-observation regions 30 located at a plurality of positions on the fluid transfer device 30.

In some embodiments, the one or more sensors 215 can be configured to determine whether there is liquid, gas (e.g., one or more bubbles), and/or a vacuum or partial vacuum, within a particular region or regions of the fluid transfer module 31 (e.g., fluid pump assembly 224). For example, as illustrated in the figures, the one or more sensors 215 can be configured to determine whether there is a medical fluid within at least a portion of the conduit 238 or whether there is a gas (e.g., ambient air or air bubbles) or a vacuum or partial vacuum within the conduit 238. In some embodiments, the one or more sensors 215 can determine whether there is a medical fluid within a portion of the conduit 238 or whether there is a gas (e.g., ambient air) or a vacuum or partial vacuum within a portion of the conduit 238. The one or more sensors 215 can be any suitable type of sensor, including but not limited to one or more acoustic sensors (e.g., ultrasonic sensors), infrared sensors, laser sensors, visual-spectrum optical sensors, motion flow sensors, or any other suitable sensors. One or more indicators 216, such as an indicator light or indicator speaker or other indicator, can be positioned on the sensor device 214 to indicate when the sensor device 214 is sensing a particular condition, such as when liquid is present in the fluid observation-region.

FIG. $2C_i$ also illustrates a fluid source container 39 in the form in this example of an inverted vial 246 attached to a vial adaptor 248 that is in turn attached to an inlet connector 32 in the form in this example of a male fluid connector 226a with a longitudinal locking mechanism. In some embodiments, the vial adaptor 248 comprises a filtered fluid inlet and/or outlet 250 and securing arms that are configured to securely receive the vial. FIG. $2C_i$ also illustrates a fluid destination container 44 in the form in this example of an IV bag 244 attached to a conduit or hose 252 (in this example by way of a bag spike 254 or other fluid connection point) that is in turn attached to the outlet connector 42 of the fluid transfer module 31. The outlet connector in FIG. $2C_i$ is in the form in this example of a male fluid connector 234a with a longitudinal locking mechanism. The IV bag 244 is suspended from the pole stand 204 by the support arm 242.

FIGS. $2A_{ii}$-$2D_{ii}$ illustrate various features, components, and arrangements that can be included in some embodiments of the fluid transfer device 30 shown in FIG. 1A and the fluid transfer system 86 shown in FIG. 1B. Similar to FIGS. $2A_i$-$2D_i$, FIG. $2A_{ii}$ illustrates an example of an electromechanical system 200 (also referred to as a fluid transfer unit 200), FIG. $2B_{ii}$ illustrates an example of a fluid transfer module 31 in the form in this example of a fluid pump assembly 224; FIG. $2C_{ii}$ illustrates the fluid pump assembly 224 of FIG. $2B_{ii}$ removably attached to the fluid transfer unit 200 of FIG. $2A_{ii}$; and FIG. $2D_{ii}$ illustrates an example of a driver 212. Unless otherwise noted, reference numerals in FIGS. $2A_{ii}$-$2D_{ii}$ refer to elements that are the same as or generally similar to the components of FIGS. 1A-$2D_i$. For example, the fluid transfer unit 200 of FIG. $2A_{ii}$ is generally similar to the fluid transfer unit 200 shown in FIG. $2A_i$, except that the one or more base supports 223 extend across an underside of the housing 202 at base support region 223a. FIG. $2C_{ii}$ also illustrates one or more trays 280 attached to the housing 202 configured to support one or more containers and/or conduits described and contemplated herein. The one or more trays 280 may comprise any one of various structures to support containers and/or conduits. For example, in some embodiments, the one or more trays 280 may comprise one or more racks with one or more slots capable of holding vials. In some embodiments, the one or more trays 280 may be configured to support a source bag and/or an IV bag, such as a saline or diluent bag and/or a bag containing therapeutic or medicinal liquid. The one or more trays 280 may be removably attached to the housing 202. In some embodiments, one tray 280 can be configured to support a saline or diluent source container and another tray 280 can be configured to support a source container with therapeutic or medicinal liquid. Among other structural differences, the supports 220 in FIG. $2A_{ii}$ are shaped differently from those shown in FIG. $2A_i$, albeit their function is the same or similar. As with all embodiments in this specification, any feature, structure, material, step, or component of any embodiment described and/or illustrated in connection with FIGS. $2A_i$-$2D_i$ can be used by itself, or with or instead of any other feature, structure, material, step, or component of any other embodiment described and/or illustrated in connection with FIGS. $2A_{ii}$-$2E_{ii}$.

As another example, FIGS. $2B_{ii}$ and $2C_{ii}$ also illustrate an example of a stopcock handle 245. In particular, FIG. $2B_{ii}$ illustrates a rear view of the stopcock handle 245 attached to the fluid pump assembly 224 and FIG. $2C_{ii}$ illustrates a front perspective view of the stopcock handle 245 attached to the fluid pump assembly 224 and removably attached to the fluid transfer unit 200. In some embodiments, the stopcock handle 245 comprises an aid for grasping the fluid pump assembly and/or positioning the fluid pump assembly 224 relative to the fluid transfer unit 200. For example, in some embodiments, the stopcock handle 245 can be configured to help position (e.g., attach, engage, remove, and/or disengage) the fluid pump assembly 224 to and/or from one or more features of the fluid transfer unit 200. The stopcock handle 245 can, for example, help engage or disengage the rotatable actuator 228 to or from the driver 212, help push the conduit 238 into or on the sensor device 214, help remove the conduit 238 from the sensor device 214, help attach or remove the actuating stem 241 to or from the receiving region of the movable platform 222, help position the one or more tabs on the syringe pump 240 on or between one or more of the protruding holders 220, help position the body of the syringe pump 240 into the one or more receptacles 218, and/or help position the body of the stopcock 230 into or on the attachment region 210, among any other suitable uses.

In some embodiments, the stopcock handle 245 can be removably attached to the stopcock 230. In some embodiments, the handle is configured to be manipulated (e.g., rotated, slid, pushed, and/or pulled) to manually actuate the stopcock into the various positions described above with reference to, for example, FIG. 1A. It will be understood that the stopcock handle 245 can be utilized in any embodiment illustrated and contemplated herein, including, for example, the embodiments shown in FIGS. 1A, 1B, and $2A_i$-$2D_i$.

FIG. $2E_{ii}$ is a rear perspective cross-sectional view of the fluid transfer unit 200 and the fluid pump assembly 224 shown in FIG. $2C_{ii}$, and illustrates various internal and external functional components. For example, as shown in FIG. $2E_{ii}$, in some embodiments, a measuring instrument such as a sensor 225 (e.g., a camera) can be positioned within the housing 202 to determine one or more features of the contents of the fluid transfer module 31 or fluid pump assembly 224, such as the volume, or type, or concentration, or color, and/or viscosity of fluid in the intermediate container or pumping region 40 (e.g., by capturing an image of the fluid transfer module 31 or fluid pump assembly 224) to provide a data file as described above. In some embodiments, a shroud 255 can be positioned adjacent to or near or generally around the one or more transparent receptacles 218 to advantageously resist the entry of undesired light from aberrant sources in order to increase the accuracy of the sensor 225. For example, in some embodiments, the shroud 255 can be configured to direct light that passes through the one or more transparent receptacles 218 toward the sensor 225, thereby increasing the amount of light available to the sensor 225. When the sensor 225 is a camera, the shroud 255 can help make the images more accurate and easier and faster to process by the processor(s) of the fluid transfer unit 200.

The fluid transfer unit 200 may comprise one or more computer processors 297, 298, which can form part of or be in electronic communication with any or all of the electromechanical controller 36 of FIG. 1A, the sensor 214, the volume sensor 225, the stopcock motor 290, and/or the platform motor 296, etc. in some embodiments, the one or more computer processors 297, 298 may comprise a pi box and/or a control board. The fluid transfer unit 200 may contain or support a power supply 295 configured to provide power to one or more components of the fluid transfer unit 200. The housing 202 may comprise a seal 293 configured to resist or prevent the entrance into and/or escape of fluid from the housing 202.

In some embodiments, the fluid transfer unit 200 may comprise one or more presence sensors 294a, 294b, 294c. The one or more sensors 294a, 294b, 294c can be positioned within and/or on the housing 202 and can determine the presence or absence of one or more structures. In some embodiments, one or more of the sensors 294a, 294b, 294c can be infrared sensors or any other suitable sensor. One or more of the sensors 294a, 294b can determine whether the fluid source container 39 (such as vial 246), the source adapter 250, and/or the source fluid connector are present and/or connected to the fluid transfer unit 200. In some embodiments, sensor 294a may determine if a source container 246 connector, such as a male or female side of a Chemolock® medical connector system, is properly engaged with a corresponding connector on the fluid transfer unit 200, such as a Chemolock® connector 226a. The sensor 294b may determine if an intermediate container 40, such as a fluid pump assembly 224, and/or connector 226a, such as a male or female side of a Chemolock® connector, is present and/or properly engaged with the housing 202 and/or a corresponding connector on a source container 246. The sensor 294c may determine whether the destination container 44, such as IV bag 244, and/or destination fluid connector are present and/or connected to the fluid transfer unit 200. In some embodiments, sensor 294c may determine if a destination container 44 connector, such as a male or female side of a Chemolock® medical connector system, is properly engaged with a corresponding connector on the fluid transfer unit 200, such as a Chemolock® connector 234a. In some embodiments, if any of sensor 294a, 294b, 294c determine that a component of the fluid transfer unit 200 is not present, the sensor 294a, 294b, 294c may send a signal to the controller 36 to prevent initiation of the fluid transfer process and/or terminate an ongoing fluid transfer. The sensor 294a, 294b, 294c may trigger an indicator signaling to a user that not all components are present or properly engaged with the fluid transfer unit 200.

As shown in FIGS. 2Ai, 2Aii, and 2Cii, in some embodiments, one or more apertures in the housing can permit one or more of the presence sensors 294a, 294b, 294c to communicate essentially or completely unimpeded from within the housing to a region outside of the housing. As illustrated, one or more of the presence sensors 294a, 294b, 294c can be positioned in substantially a collinear manner with each other and/or with the primary longitudinal axis of the fluid transfer module 31 (e.g., presence sensors 294a, 294b), and/or one or more other of the presence sensors 294a, 294b, 294c can be positioned in a non-collinear manner or at an angle or perpendicular to the primary longitudinal axis of the fluid transfer module 31 (e.g., presence sensor 294c). In some embodiments, as shown, one or more or all of the sensors are positioned and/or recessed inside of the housing of the electronic fluid transfer system, such that a panel through which the sensors are configured to detect items is essentially or substantially or entirely planar. As illustrated, one or more of the sensors does not include and/or is not attached by any external wires outside of the housing of the electronic fluid transfer system.

In some embodiments, one or more of the sensors 294a, 294b, 294c can be configured to detect the presence or absence of at least a portion of a fluid transfer module attached to the electronic fluid transfer device, such as a connector on the fluid transfer device. In some embodiments, one or more of the sensors (e.g., 294a, 294b) can be configured to additionally or alternatively detect the presence or absence of or connection with at least a portion of a fluid source system, such as a connector or vial adaptor or vial or bag or conduit that forms part of or is connected to a fluid source system. In some embodiments, one or more of the sensors (e.g., 294c) can be configured to additionally or alternatively detect the presence or absence of or connection with at least a portion of a fluid destination system, such as a connector or bag or conduit that forms part of or is connected to a fluid destination system. In some embodiments, the detection of one or more of the fluid transfer module 31, the detection of the connection to the fluid source system, and/or the detection to the connection to the fluid destination system can be a gating step or a required step for the computer processor or other component of the electro-mechanical controller to permit fluid transfer to begin or continue.

FIG. 3 illustrates a user interface 78 that can be used with the fluid transfer unit 200 in the form in this example of a remote tablet. The user interface 78 can comprise a rechargeable internal battery, a touch-sensitive screen to enable user selection and input by way of the screen, and one or more additional or alternative user inputs 256, such as a button (as shown) or a knob or a slider or a rocking switch, or a rolling dial, or any other user input. The user interface 78 can communicate electronically with one or more fluid transfer units 200 and/or with one or more patient and/or drug information storage devices or networks 70 utilizing any suitable electronic protocols or electronic communicators. In some embodiments, the user interface 78 is fixed to the fluid transfer unit 200, such as being attached to or contained at least partially within the housing of the fluid transfer unit 200.

The user interface 78 can display or convey various items of information between a user and an electronic storage medium and/or can convey one or more executable instructions to a computer processor in the fluid transfer unit 200, or to electromechanical hardware in the fluid transfer unit 200, to perform one or more actions relating to fluid transfer. For example, the user interface 78 can receive and/or store (e.g., by user input or electronic transmission) the identity of the pharmacist or technician who is performing the fluid transfer, the identity of the patient, the name of the medical fluid, the volume of medical fluid to be transferred, the lot number, the expiration date of the medical fluid, and/or the date and time on which the fluid transfer was performed, etc. Also, as other examples, the user interface 78 can assist in controlling the fluid transfer by receiving and conveying commands from the user via the user interface 78 and/or displaying messages from the fluid transfer unit 200 regarding the progress and/or status of the fluid transfer, such as commands initiating the fluid transfer and/or halting the fluid transfer, and/or one or more messages demonstrating the amount of fluid transferred at any given moment, or the history of fluid transfers for a particular patient or pharmacist over a particular period, or one or more error messages indicating that the fluid transfer was not completed or that the fluid source container 39 is not connected or is empty, or the fluid destination container 44 is not connected or is full, or any other useful message.

FIG. 4 illustrates an example of a fluid transfer management system 74 in the form in this example of an integrated fluid transfer unit 50 that includes a user interface 78 as an integrated touch screen 76 attached in the housing 52 of the fluid transfer unit 50. In this example, a fluid transfer module 31 is held in a generally horizontal manner next to a support platform 58. In some embodiments, the support platform comprises part of the housing 52. The fluid transfer module 31 is provided in the form in this example of a syringe pump attached via a connector 300 to a multidirectional flow-control valve 41 in the form in this example of a fluid stopcock 230 with an actuator in the form in this example of one or more protruding arms. The stopcock 230 is attached in selective fluid communication with a source container 39 in the form in this example of an inverted vial 246 and a destination container 44 in the form in this example of an IV bag 248. A driver 212 on the fluid transfer management system 74 is provided in the form in this example of a forked or slotted or grooved interface 60 configured to receive or attach to or couple with, and to drive, one or more of the protruding arms on a rotating actuator of the stopcock 230. The interface 60 is configured to rotate the rotating actuator to select one of a plurality of fluid communication positions, as in any other embodiments disclosed in this specification. The IV bag 248 can be supported, as shown, on a generally horizontal tray 56 attached to the integrated fluid transfer unit 50. As with all embodiments in this specification, any feature, structure, material, step, or component of the device illustrated and/or described in connection with FIG. 4 can be used with or instead of any feature, structure, material, step, or component of any other device that is illustrated and/or described elsewhere in this specification.

FIG. 5 illustrates an example of a fluid transfer module 31 in the form in this example of a positive displacement system 275 that can be provided for use in a fluid transfer management system 74 that includes a positive displacement pump, such as a peristaltic pump (see, e.g., FIGS. 6 and 6a). The positive displacement system can include an inlet fluid connector 226, such as a closeable male luer connector, a conduit 227 extending between the fluid connector 226 and a first channel of a multidirectional flow-control valve 41 in the form in this example of a fluid stopcock 230 that includes an interface configured to be coupled to or attach with or interface with a driver on an electromechanical controller 36 of a fluid transfer system 86. In some embodiments, the conduit 227 is substantially shorter than as illustrated and can be essentially just a short region of contact between the inlet connector 226 and the stopcock 230, or the conduit 227 can be omitted and the inlet connector 226 can essentially attach directly to the stopcock 230.

A second channel of the stopcock 230 can be attached to an intermediate or measuring region 268 by way of a first conduit segment 260, a positive displacement conduit segment 270, and a second conduit segment 264. One or more coupling regions 262, 266 can be provided between the first conduit segment 260 and the positive displacement conduit segment 270, and between the positive displacement conduit segment 270 and the second conduit segment 264, and/or between the second conduit segment 264 and the intermediate or measuring region 268, as illustrated in FIG. 5. The positive displacement conduit segment 270 can be form of a polymer material that is softer, less rigid, more flexible, and/or of a lower durometer than either or both of the materials of which the first and second conduit segments 260, 264 are made. A third channel of the stopcock 230 can be attached to an outlet fluid connector 226, such as a closeable male connector, by way of an outlet conduit 268 and one or more other male or female connectors 226, 229, or the third channel of the stopcock 230 can be directly attached to an outlet fluid connector 226 with a short connector or otherwise.

A source container 39 is illustrated in FIG. 5 in the form in this example of an inverted vial 246 with a vial adaptor that includes a closeable female fluid connector 249 that is configured to attach to the inlet connector 226. A destination container 44 is illustrated in the form in this example of an IV bag 248 with an inlet port 250 (such as an integrated port with a fluid connector, such as a closeable female fluid connector 229, as shown, or a spike-receiving septum or any other suitable inlet port).

As shown in FIG. 6, the fluid transfer module 31 or positive displacement system 275 of FIG. 5 can be part of a fluid transfer system 86 in the form in this example of a positive displacement fluid transfer unit 1318 when the fluid transfer module 31 is removably coupled with the fluid transfer unit 1318. The inverted vial 249 can be supported by the pole stand 204 and the IV bag can be supported by the tray 56. A stopcock driver 263 of the positive displacement fluid transfer unit 1318 can be configured to receive and functionally interface with the stopcock 230 to actuate the stopcock 230, such as by rotating or otherwise moving an actuator on the stopcock 230, to select among the different channels of the stopcock 230. An integrated user-visible screen can be permanently or removably attached to the fluid transfer unit 1318. As with all embodiments in this specification, any feature, structure, material, step, or component of the positive displacement fluid transfer unit 1318 can be used with or instead of any feature, structure, material, step, or component of any other fluid transfer unit 50, 200, 1318a.

A positive displacement pump 1350 can be configured to receive the intermediate container or pumping region 40 in the form in this example of a positive displacement segment 270 of the positive displacement system 275. In some embodiments, the positive displacement pump 1350 is a peristaltic pump or another type of pump that includes one or more advancing fluid-pushing structures comprising one or more rotating or sliding or otherwise moving arms or wipers or rollers or kneaders or rotors that can be configured during use to constrict, pinch, occlude, squeeze, and/or compress a portion of the positive displacement segment 270 in a progressive or linear manner along the positive displacement segment 270 to forcefully advance or express an amount of fluid contained within the positive displacement segment 270 either upstream (toward the source container 39) or downstream (toward the destination container 44). Many other types of pumps can be used to move fluid forward or backward within the positive displacement segment 270.

In some embodiments, the fluid transfer unit 1318 can include a volume sensor 225 that is configured to provide information to help calculate the volume of liquid in the intermediate or measuring region 268. The volume sensor 225 can include any appropriate sensor or combination of sensors to provide information about the volume of the liquid, such as an optical sensor (such as a camera or a break-beam sensor), an infrared sensor, an acoustic sensor (e.g., an ultrasonic sensor), and/or a mass or weight sensor, etc. In some embodiments, the volume sensor can be internal and/or external to the fluid transfer unit 1318. In any embodiments in this specification, the tray 280, 56 or the support arm 242 or the pole stand 204 or any other support structure that holds or supports or contains any form of the destination container 44 and/or any form of the intermediate container or pumping region 40 can include any one of, or any combination of, any such sensors to help provide information about any characteristic of the liquid that has been transferred into the destination container 44, such as information about the volume, mass, weight, and/or any other characteristic of the transferred liquid. The computer processor can comprise one or more algorithms, subroutines, hardware, and/or program instructions configured to process one or more signals received from one or more of such sensors to calculate information regarding one or more of the liquid characteristics.

FIG. 6a illustrates an example of another type of positive displacement fluid transfer unit 1318a. As with all embodiments in this specification, any feature, structure, material, step, or component of the positive displacement fluid transfer unit 1318 can be used with or instead of any feature, structure, material, step, or component of the positive displacement fluid transfer unit 1318a. In some embodiments, the positive displacement fluid transfer unit 1318a comprises a fluid transfer device, as shown, that is physically separated from the user interface 78. For example, the positive displacement fluid transfer unit 1318a can be used with a remote user control device, such as user interface 74 of FIG. 3. In some embodiments, the fluid transfer module of the positive displacement fluid transfer unit 1318a can comprise a first source fluid connector 226, a gas sensing region 231, a positive displacement conduit segment 270, and a second destination fluid connector 226.

As illustrated, the fluid transfer module need not include an intermediate container and/or the fluid transfer module need not include a multidirectional flow-control valve; rather, the liquid from the source container 39 or vial 246 can be pumped or transferred directly into the destination container 44 or IV bag 248 (e.g., via the associated tubing and connectors of the fluid transfer module) by the positive displacement motion of the positive displacement pump 1350. The gas sensing region 231 of the fluid transfer module can be coupled with a gas sensor assembly 265 that is configured to sense whether gas (such as air) in a bubble or otherwise has entered into the fluid transfer module.

FIG. 7 illustrates an example of a fluid transfer process 600. An advantage of some embodiments of this fluid transfer process 600 is that a high-precision dosage of liquid can be transferred to the destination container by carefully controlling and monitoring when a gas, such as air, enters the liquid pathway within one or more conduits of the fluid transfer module 31, and then by removing the gas from the liquid pathway and/or not counting any transferred gas in the destination container 44 as a transferred liquid. As with all embodiments in this specification, one or more of the steps of the fluid transfer process 600 can be performed alone, in one or more groups, or in a different ordering than is illustrated in FIG. 7 and/or than is described herein. Chronological terms such as "before" or "after" or "begin" or "start" or "end," or any similar terms, are provided only as examples and are not required in all embodiments. None of these steps is essential or indispensable.

The fluid transfer process 600 begins at the start block 602. If a fluid transfer module 31 in the form in this example of a connector assembly (e.g., a multi-stroke pump assembly 224 or a positive displacement system 275, etc.) has not already been attached to a source container 39, then the source container 39 is attached to the connector assembly at block 604. If the connector assembly has already been attached to a source container 39 (or if it will be attached later), then the connector assembly is attached to a fluid transfer management system 74 in the form in this example of an electronic fluid-delivery device, such any of the fluid transfer units 50, 200, 1318, 1318a, or any other type of fluid transfer unit, at block 605.

In some situations, the connector assembly has previously been in use, such as when only a portion of the fluid in a source container 39 of a first connector assembly has been withdrawn but the connector assembly is temporarily disconnected or removed from the fluid transfer management system 74 to permit a second connector assembly attached to a source container 39 with a different type of therapeutic liquid to be coupled with the fluid transfer management system 74 for another type of fluid transfer. After the second connector assembly is used in the fluid transfer management system 74, the first connector assembly can be reattached in its original position in order to withdraw all or a portion of the remaining contents of the source container 39. Thus, in this example, among others, the first connector assembly has previously been in use.

If the connector assembly has not already been used, then in some instances the connector assembly can be "primed" at block 100 by filling the connector assembly with liquid and by removing gas, such as air, from the connector assembly. Priming may comprise filling the interior cavity of connector 234 and/or connecter 226 prior to transferring of fluid to a destination container 44. In some situations, gas needs to be removed from the connector assembly to avoid transferring air into a destination container 44 that will be transferred entirely into a patient's blood vessel. For example, priming may be useful where it is desirable to remove any clinically significant amount of air prior to transferring of fluid to a destination container 44, such as a syringe containing liquid that will be injected directly into a patient or into a patient's fluid line. In some situations, such as when an IV bag 248 is used, the concern of harming the patient 44 is not as severe, since an IV bag 248 is typically gravity-fed and the gas migrates to the top of the bag without entering the patient's blood vessel anyway. In some instances, the main concern is that a transfer of gas from the connector assembly into the destination container 44 might be mistakenly counted as a transfer of therapeutic liquid into the destination container 44, which may result in an undercount of the amount of therapeutic liquid provided to the patient, or it may lower the concentration of therapeutic liquid provided to the patient. In some embodiments, any one and/or all of the concerns may be resolved through various methods described in further detail below. An example of the priming process is illustrated and described more fully in FIG. 8A. Another example of a priming process is illustrated and described in FIG. 8B. After the connector assembly is primed, it can be connected to the destination container 44 at block 610.

If the connector assembly has already been used, then the connector assembly does not need to be filled with liquid or primed. However, the connector assembly may have acquired air bubbles inside of it, such as during the disconnection process, or from partial vaporization of the liquid within the connector assembly, or by partial external spillage. The air bubbles can be substantially or entirely removed during a purging step in block 608, which is explained more fully in connection with block 123 of FIG. 8A or block 123' of FIG. 8B. After the connector assembly has been purged of gas, it can be attached to the destination container 44 at block 610.

After the source container 39 and the destination container 44 are attached to the fluid transfer module 31 (or connector assembly), the fluid transfer device 30 can proceed to transfer fluid from the source container 39, through the fluid transfer module 31, to the destination container 44, which is illustrated and explained more fully in FIG. 9. Once the fluid transfer is complete, the destination container 44 can be detached from the fluid transfer module 31 and transported to the patient for administration of the therapeutic fluid.

An example of the process of priming and purging is illustrated more fully in FIG. 8A or FIG. 8B. Each of the steps illustrated and/or described in connection with FIGS. 7-9 can be performed or controlled or actuated, in whole or in part, by the computer processor positioned in or associated with the fluid transfer management system 74. The computer processor can be attached in electrical communication with the patient and/or drug information storage device(s) or network(s) 70, user interface 78, the memory 84 or memories 84, the electromechanical controller 36, and/or the electromechanical driver. The computer processor can include, or can communicate with one or more memories or other electronic media that include, software or hardware instructions or subroutines or algorithms for performing any or all of the steps illustrated or described in this specification, including the steps illustrated in FIGS. 7-9. The steps shown in FIGS. 7-9 can be performed in the order illustrated, or in any other order, or individually or in one or more groups, as may be useful. The particular ordering illustrated in these figures is merely one example of many and should not be understood to be limiting. Any of the steps can be changed or omitted, and one or more additional steps can be included. For example, in embodiments involving positive displacement fluid transfer units 1318, 1318a, such as those illustrated in FIGS. 6 and 6a, some of the steps can be different or omitted.

As previously discussed, priming sequences detailed in FIGS. 8A and 8B may not be utilized in all instances of the fluid transfer process. In FIG. 8A, at the beginning in block 106, the multidirectional flow-control valve 41 (such as a fluid stopcock 230) can be mechanically actuated by the electromechanical controller 36 of the fluid transfer device 30 (such as via the computer processor) to close an inlet port on the fluid-control valve 41 (e.g., an inlet port directly connected to an inlet conduit 232 in fluid communication with the source container 39), and to open simultaneously or generally concurrently a fluid pathway between an outlet port on the fluid-control valve 41 (e.g., an outlet port directly connected to an outlet fluid connector 42) and an intermediate outlet port on the fluid-control valve 41 (e.g., an intermediate outlet port directly connected to an intermediate conduit 236 and to the intermediate container 40). The outlet connector 42, fluid-control valve 41, and intermediate container 40 can then be positioned in fluid communication with each other, while the source container 39 can be isolated or not in fluid communication with these components. An example of this configuration 108 shows an inverted vial 246 attached to a stopcock 230 by way of a male fluid connector 226 that is blocked from fluid communication with the stopcock 230 and other components, while a syringe pump 240 attached to the stopcock 230 is in fluid communication through the stopcock 230 with the outlet fluid connector 234.

At block 110, the intermediate container 40 can be actuated (such as by exerting a pulling force on the actuating stem 241 of a syringe pump 240) to expand or increase the volume within the intermediate container 40, thereby lowering the pressure or creating at least a partial vacuum within the intermediate container 40, which can also lower the pressure or create at least a partial vacuum within the fluid control valve 41 and the outlet connector 42. The intermediate container 40 can be actuated by an electronic signal or series of signals sent from the computer processor of the fluid transfer management system 74 to an electromechanical driver in the fluid transfer management system 74 that is configured to be removably linked to or mechanically connected (either directly or indirectly) with the intermediate container 40 by way of a moveable actuator. For example, the electromechanical driver can be a motor, such as a stepper motor, that is mechanically linked to a moveable actuator in the form in this example of the movable platform 222 of the fluid transfer unit 200. As illustrated in FIG. 2C$_i$, the syringe stem 246 can be received into a recess or other retainer on the movable platform 222. The movable platform 222 may be controlled via a platform motor 296, as shown in FIG. 2E$_{ii}$. The platform motor may comprise the movable platform 222 and/or any portion that extends outward from the housing 202. The electromechanical controller 36 may send a signal activating the platform motor 296, as shown in FIG. 2E$_{ii}$, to initiate movement of the movable platform 222. As illustrated in configuration 112, the computer processor can send a signal or series of signals to the electromechanical driver to actuate the movable platform 222 to pull downward or extend outwardly the actuating stem 241 of the syringe pump 240. As shown in block 110, the actuation of the syringe pump 240 in this configuration 112 can lower the pressure or create a partial vacuum within the outlet port and the syringe pump 240.

At block 114, the computer processor of the fluid transfer management system 74 can send an electronic signal to the electromechanical controller 36 of the fluid transfer device 30 to mechanically actuate the multidirectional flow-control valve 41 to close an outlet port on the fluid-control valve 41 (e.g., an outlet port directly connected to an outlet conduit 236 that is configured to be placed in fluid communication with the destination container 44), and to open simultaneously or generally concurrently a fluid pathway between the inlet port on the fluid-control valve 41 and the intermediate outlet port on the fluid-control valve 41. The closing of the outlet port seals off and preserves the lower pressure or partial vacuum within the outlet conduit 236 and the outlet fluid connector 42 or outlet male fluid connector 234. The inlet connector 32 (and source container 39), fluid-control valve 41, and intermediate container 40 can then be positioned in fluid communication with each other, while the outlet connector 42 can be isolated or not in fluid communication with these components. An example of this configuration 116 shows an inverted vial 246 attached to a stopcock 230 by way of a male fluid connector 226 that is in fluid communication with the stopcock 230 and the syringe pump 240, while the male fluid connector 234 attached to the outlet port and outlet conduit 236 is blocked from fluid communication with the stopcock 230 and other components.

As illustrated, when the fluid-control valve 41 or stopcock 230 is actuated as illustrated in block 114, fluid from the source container 39 rapidly flows into the multidirectional flow control valve 41 or stopcock 230 and the intermediate container 40 or syringe pump 240, since the pressure in the source container 39 is higher than the pressure of the partial vacuum within the flow control valve 41 and the intermediate container 40. In some embodiments, after the migration of fluid from the source container 39 to the flow-control valve 41 and intermediate container 40, only a small amount of air bubbles or a small air region is present in the intermediate container 40. The air region or air bubbles generally migrate upward within the syringe pump 240, since the air is less dense than the fluid transferred from the source container 39, which is typically liquid. Additional air may still be present within the flow control valve 41.

At block 118, the computer processor of the fluid transfer management system 74 can send an electronic signal to the electromechanical controller 36 of the fluid transfer device 30 to mechanically actuate the electromechanical driver. In some embodiments, as illustrated, the actuation of the electromechanical driver can upwardly move the movable platform 222 and push the actuating stem 241 into the syringe pump 240, thereby decreasing the volume and increasing the pressure within the intermediate container 40 or syringe pump 240 to urge or push liquid and any accompanying air within the intermediate container 40 or syringe pump 240 backward or in reverse from the intermediate container 40 or syringe pump 240 into the flow-control valve 41, the inlet connector 226, and the source container. This reverse or backward flow of liquid can help to "prime" the fluid pathway between the source container 39, the flow control valve 41, and the intermediate container 40, to remove all or a portion of the air within or between these components to enable it to later be replaced with liquid. For example, when the air is pushed into or returned to the source container 39 by the reverse or backward flow, the air migrates to the top of the inside of the source container 39, since its density is lower than that of the surrounding liquid, and when the intermediate container 40 is actuated to pull fluid back into it, the liquid at the bottom of the source container 39 moves through the inlet connector 226 and associated structures into the intermediate container 40, rather than the air.

At block 120, the computer processor of the fluid transfer management system 74 can send an electronic signal to the electromechanical controller 36 of the fluid transfer device 30 to mechanically actuate the multidirectional flow-control valve 41 to close an outlet port on the fluid-control valve 41 (e.g., an outlet port directly connected to an outlet conduit 238 in fluid communication with the intermediate container 40), and to open simultaneously or generally concurrently a fluid pathway between the inlet port on the fluid-control valve 41 (in fluid communication with the source container 39) and the outlet port on the fluid-control valve 41 that is in fluid communication with the outlet fluid connector 42. An example of this configuration 122 shows the inverted vial 246 in fluid communication with the stopcock and the outlet fluid connector 42, but not the syringe pump 240.

In some embodiments, in one or more previous steps such as at blocks 110 and 114, the air within the outlet port and outlet fluid connector 42, and the associated conduit(s), has been evacuated or the pressure within these components has been diminished, and then the interior regions of these components has been sealed off or isolated by actuating the flow-control valve 41, in order to close the fluid pathway inside of these components from one or more or all of the other components of the fluid transfer module 31. When the multidirectional flow-control valve 41 is actuated at block 120 to open the outlet port, the outlet fluid connector 42, and/or the associated tubing, to be in fluid communication with the flow-control valve 41 and the source container 39, then liquid from the source container 39 rapidly flows through the flow-control valve 41 or stopcock 230 and into the outlet fluid connector 42, since the pressure in the source container 39 and the flow-control valve 41 is much higher than the pressure of the partial vacuum within the outlet fluid connector 42 and there is very little air to block the entering liquid. This process can prime the outlet fluid connector 42 and its associated tubing (such as conduit 238), without producing air bubbles or without producing an unduly or unmanageably large amount of air bubbles in the fluid pathway.

At this point, the fluid transfer module 31 is usually primed, in that all or substantially all of the gas or air has been removed from the fluid transfer module 31 and replaced with liquid from the source container 39. In this context, "substantially" all of the gas or air or any similar phrase should be understood to mean that enough gas or air has been removed that no clinically significant imprecise measurements or other adverse results would be caused by any remaining gas or air. Referring back to FIG. 7, the priming step at block 100 is now completed in this example (although other examples can include less or more or other steps or sequences), and the destination container 44 (such as an IV bag) can be coupled in fluid communication with the fluid transfer module 31 by way of the outlet fluid connector 234.

At block 123, the computer processor of the fluid transfer management system 74 can send an electronic signal to the electromechanical controller 36 of the fluid transfer device 30 to mechanically actuate the multidirectional flow-control valve 41 to close the outlet port on the fluid-control valve 41 that is in fluid communication with the outlet connector 234, and to open simultaneously or generally concurrently a fluid pathway between the inlet port on the fluid-control valve 41 that is in fluid communication with the source container 39 and the outlet port on the fluid-control valve 41 that is in fluid communication with the intermediate container 40. An example of this configuration 123 shows the inverted vial 246 in fluid communication with the stopcock and the syringe pump 240 but not the outlet fluid connector 42. At this point, the computer processor can send a signal or series of signals to the electromechanical movable platform 222 to actuate the syringe pump 240 to draw in the proper amount of therapeutic fluid to be transferred to the destination container 44.

FIG. 8B provides an embodiment of some priming steps sequence that may be utilizing by the fluid transfer unit 200. At block 114', the computer processor of the fluid transfer management system 74 can send an electronic signal to the electromechanical controller 36 of the fluid transfer device 30 to mechanically actuate the multidirectional flow-control valve 41 to close an outlet port on the fluid-control valve and open a fluid pathway between the inlet port on the fluid-control valve 41 and the intermediate outlet port on the fluid-control valve 41. The inlet connector 32 (and source container 39), fluid-control valve 41, and intermediate container 40 can then be positioned in fluid communication with each other, while the outlet connector 42 can be isolated or not in fluid communication with these components. An example of this configuration 116' shows an inverted vial 246 attached to a stopcock 230 by way of a male fluid connector 226 that is in fluid communication with the stopcock 230 and the syringe pump 240, while the male fluid connector 234 attached to the outlet port and outlet conduit 236 is blocked from fluid communication with the stopcock 230 and other components.

In some embodiments, when the fluid-control valve 41 or stopcock 230 is actuated, the fluid transfer management system 74 at block 118' may actively transfer fluid into the intermediate container 40 or syringe pump 240. The computer processor of the fluid transfer management system 74 can send an electronic signal to the electromechanical controller 36 of the fluid transfer device 30 to mechanically actuate the electromechanical driver. In some embodiments, as illustrated in 116', the actuation of the electromechanical driver can downwardly move the movable platform 222 and pull the actuating stem 241 out of the syringe pump 240, thereby increasing the volume and decreasing the pressure within the intermediate container 40 or syringe pump 240 to urge or pull liquid within the source container 39 into the intermediate container 40 or syringe pump 240. In some embodiments, after the migration of fluid from the source container 39 to the flow-control valve 41 and intermediate container 40, a small amount of air bubbles or a small air region may be present in the intermediate container 40. The air region or air bubbles generally migrate upward within the syringe pump 240, since the air is less dense than the fluid transferred from the source container 39, which is typically liquid. Additional air may still be present within the flow control valve 41.

At block 118", the computer processor of the fluid transfer management system 74 can send an electronic signal to the electromechanical controller 36 of the fluid transfer device 30 to mechanically actuate the electromechanical driver. In some embodiments, as illustrated, the actuation of the electromechanical driver can upwardly move the movable platform 222 and push the actuating stem 241 into the syringe pump 240, thereby decreasing the volume and increasing the pressure within the intermediate container 40 or syringe pump 240 to urge or push liquid and any accompanying air within the intermediate container 40 or syringe pump 240 backward or in reverse from the intermediate container 40 or syringe pump 240 into the flow-control valve 41, and the inlet connector 226. This reverse or backward flow of liquid can "prime" the fluid pathway between the source container 39, the flow control valve 41, and the intermediate container 40, to remove all or a portion of the air within these components and replace it with liquid. The backward flow of liquid may remove any air present in the syringe pump 240, thereby preventing the later transfer of air to the outlet port, outlet conduit 236, and/or outlet container. The movable platform 222 may be positioned to inject sufficient flow of fluid into the source container 39 to prime the fluid pathway between the source container 39, the flow control valve 41, and the inlet connector 226, while maintaining an amount of fluid within the intermediate container 40 sufficient to prime the outlet connector 42. The amount of liquid to prime the outlet connector 42 may include a volume of liquid about at least equal to the volume of the interior cavity of the outlet connector 42.

At the beginning in block 106', the multidirectional flow-control valve 41 can be mechanically actuated by the electromechanical controller 36 of the fluid transfer device 30 to close an inlet port on the fluid-control valve 41 and open simultaneously or generally concurrently a fluid pathway between an outlet port on the fluid-control valve 41 and an intermediate outlet port on the fluid-control valve 41. The outlet connector 42, fluid-control valve 41, and intermediate container 40 can then be positioned in fluid communication with each other, while the source container 39 can be isolated or not in fluid communication with these components. An example of this configuration 108' shows an inverted vial 246 attached to a stopcock 230 by way of a male fluid connector 226 that is blocked from fluid communication with the stopcock 230 and other components, while a syringe pump 240 attached to the stopcock 230 is in fluid communication through the stopcock 230 with the outlet fluid connector 234.

Block 106' and 106" may evacuate any air within the outlet port and outlet fluid connector 42 or diminish the pressure within these components. The computer processor of the fluid transfer management system 74 can send an electronic signal to the electromechanical controller 36 of the fluid transfer device 30 to mechanically actuate the electromechanical driver. In some embodiments, the actuation of the electromechanical driver can downwardly move the movable platform 222 and pull the actuating stem 241 out of the syringe pump 240, thereby increasing the volume and decreasing the pressure within the intermediate container 40 or syringe pump 240 to urge or pull liquid and any accompanying air within the outlet port and outlet fluid connector 42 into the intermediate container 40 or syringe pump 240. This reverse or backward flow of liquid can "prime" the fluid pathway between the destination container, the outlet port, and the outlet fluid connector 42, to remove all or a portion of the air within these components and replace it with liquid. In some embodiments, as illustrated in block 106", the actuation of the electromechanical driver can upwardly move the movable platform 222 and push the actuating stem 241 into the syringe pump 240, thereby decreasing the volume and increasing the pressure within the intermediate container 40 or syringe pump 240 to urge or push liquid within the intermediate container 40 or syringe pump 240 into the outlet port and outlet fluid connector 42. This flow of liquid can prime the fluid pathway between the destination container, the outlet port, and the outlet fluid connector 42, to remove all or a portion of the air within these components and replace it with liquid.

At block 123', the computer processor of the fluid transfer management system 74 can send an electronic signal to the electromechanical controller 36 of the fluid transfer device 30 to mechanically actuate the multidirectional flow-control valve 41 to close the outlet port on the fluid-control valve 41 that is in fluid communication with the outlet connector 234, and to open simultaneously or generally concurrently a fluid pathway between the inlet port on the fluid-control valve 41 that is in fluid communication with the source container 39 and the outlet port on the fluid-control valve 41 that is in fluid communication with the intermediate container 40. An example of this configuration 123' shows the inverted vial 246 in fluid communication with the stopcock and the syringe pump 240 but not the outlet fluid connector 42. At this point, the computer processor can send a signal or series of signals to the electromechanical movable platform 222 to actuate the syringe pump 240 to draw in the proper amount of therapeutic fluid to be transferred to the destination container 44.

If, at any other stage of FIGS. 8A and/or 8B, the sensor 215 detects that a gas or air bubble or a significant amount of gas or air is located somewhere in the fluid transfer module 31 (such as in the fluid-observation region of the conduit 238), a sequence of one or more steps constituting a "gas purge" can be performed. A "significant amount of gas" is any amount of gas that would yield clinically significant imprecise measurements or other adverse results if permitted to remain in the fluid transfer module 31 or if permitted to be transferred into the destination container 44. In some embodiments, as part of the purging process, an electrical signal can be sent from the sensor 215 to the computer processor indicating detection of gas. Another electrical signal or a series of electrical signals can be sent from the computer processor to the electromechanical driver to move the movable platform 222 down to draw an amount of liquid from the source container 39 into the flow-control valve 41 and into the intermediate container 40, and then an electrical signal or a series of electrical signals can be sent from the computer processor to the electromechanical driver to move the movable platform 222 up to push an approximately equal amount of liquid out of the intermediate container 40 up through the flow-control valve 41 and back into the source container 39, and then another electrical signal or a series of electrical signals can be sent from the computer processor to the electromechanical driver to move the movable platform 222 down again to draw an amount of liquid from the source container 39 into the flow-control valve 41 and into the intermediate container 40.

This back-and-forth or drawing-and-expelling movement of liquid between the source container 39 and the intermediate container 40 can help to purge air from the fluid transfer module 31 because any air present will normally rise to the top of the central chamber of the intermediate container 40, or the top of the conduit 238, or the top of the fluid-control valve 41, and/or the top of the conduit 232 (since the gas or air is less dense than the liquid surrounding it), and then the gas or air can be returned or moved into the source container 39 during the return stroke before the liquid in the central chamber of the intermediate container 40 is returned or moved into the source container 39. If a first iteration of the back-and-forth or drawing-and-expelling movement does not sufficiently purge any significant amount of air from the fluid transfer module 31, then a second iteration or a plurality of additional iterations of the back-and-forth or drawing-and-expelling movement can be performed.

Any single step or grouping of steps of FIG. 8A and/or FIG. 8B can be used with a different type of pump (other than a syringe pump 240), such as a positive displacement fluid transfer unit 1318, 1318a, as illustrated in FIGS. 6 and 6a, with appropriate modifications as needed. For example, in a method of transferring fluid using the positive displacement fluid transfer unit 1318a of FIG. 6a, in which there is no intermediate container 40, many or most of the steps of FIG. 8A or 8B can be omitted. In some embodiments, priming can be accomplished in such a pump by simply drawing liquid from the source container 39 into the destination container 44 with a forward motion of the positive displacement pump 1350 under the control of one or more electrical signals from the computer processor. If any gas or air bubbles is or are detected by the gas sensor assembly 265, such as through the gas sensing region 231 of the fluid transfer module, then the computer processor can send one or more electrical signals to the positive displacement pump 1350 to reverse direction for a predetermined number of steps or rotations of the pump 1350 and/or for a predetermined period corresponding to the time required to pump the gas or air back into the fluid source container 39. Multiple iterations of a back-and-forth motion can be used as appropriate to eliminate any significant amount of gas.

As illustrated in the example of FIG. 9, the process of transferring fluid as shown at block 500 of FIG. 7 can be performed by starting at block 502, in which the fluid transfer module 31 can be configured as shown in block 123 of FIG. 8A and/or in configuration 104 of FIG. 8A, in some embodiments. The process of transferring a quantity of fluid from the source container 39 toward the intermediate container 40, as shown in block 506 of FIG. 9, can be accomplished in some embodiments as follows: the computer processor can send an electronic signal or a series of electronic signals to the electromagnetic driver to move the moveable platform 222 down, which can pull on the actuating stem 241 to increase the volume inside of the internal fluid chamber of the syringe pump 240, which lowers the pressure inside of the syringe pump 240 and urges liquid from the source container to flow through the stopcock 230 and into the syringe pump 240. In a positive displacement pump, such as the positive displacement pumps 1350 of FIGS. 6 and 6a, the computer processor can send an electronic signal or a series of electronic signals to the positive displacement pump 1350. In some embodiments in which the electromagnetic driver is a stepper motor, the computer processor can send a series of pulses (or one or more other appropriate signals) corresponding to a number of discrete steps to be made by the stepper motor that correspond to a particular volume of fluid to be transferred by such steps in the syringe pump 240.

After or during the transfer of fluid at block 506, the sensor 215 can constantly or intermittently monitor one or more regions of the fluid transfer module 31, such as a fluid-observation region on the conduit 238, to determine whether a gas, such as air, is present or has migrated into the fluid transfer module 31, as represented at block 510. If a significant gas bubble is detected (e.g., a gas bubble that is approximately equal to or greater than 0.1 mL, or approximately equal to or greater than 0.25 mL, or approximately equal to or greater than 0.5 mL, etc.), then the computer processor can query a memory 84 in the fluid transfer management system 74 at block 508 to determine whether a purge of such gas bubble (or a predetermined plurality of purges, such as two purges or three purges, or more) has already been performed during this particular stage in the fluid transfer process. If a purge or a predetermined plurality of purges has not yet been performed at this stage in the fluid transfer, then a gas purge can be performed at block 504. The gas purge can be performed according to any or a portion of the procedures or steps described in this specification, or according to one or more additional or alternative procedures or steps. After the gas purge is completed, the computer processor can return to block 506 by sending an electronic signal or a series of electronic signals to the electromagnetic driver to transfer a quantity of liquid from the source container 39 to the intermediate container 40. If a purge or a predetermine plurality of purges has been performed at this stage in the fluid transfer, then the computer processor proceeds to block 514 and stops the transfer of liquid and displays an error message to the user.

The error message can communicate to a user than the vial is presumed to be empty and should be replaced with a full vial since no liquid is passing from the source container 39 into the intermediate container 40 and/or the error message can communicate one or more other messages, such as a message encouraging the user to check the fluid couplings in the fluid transfer device 30.

If the vial is replaced, then the computer processor can proceed to block 605 of FIG. 7, in which case the sum of any liquid already transferred in one or more previous iterations at block 506 of FIG. 9 will be retained in the memory 84 and added to upon subsequent transfers of liquid. When such a replaced source container 39 and fluid transfer module 31 is reattached to the fluid transfer management system 74, then the query of memory 84 at block 606 will confirm that the fluid transfer module 31 (or connector assembly) has already been used and the computer processor will proceed to purge the fluid transfer module 31 at block 608 rather than priming it at block 100 (since it has already been primed). During the transfer of fluid between the intermediate container 40 or syringe pump 240 to the destination chamber 44, the electromagnetic driver configured to move the moveable platform 222 may be used in combination with the sensor 215 as a flowmeter to measure the rate of flow and calculate the total amount of fluid transferred into the destination chamber 44. The combination of the electromagnetic driver and sensor 215 may function as a volumetric device. As discussed above, the sensor 215 may monitor one or more regions of the fluid transfer to determine whether a gas is present. The electromagnetic driver may transfer a set volume of fluid. When used in combination, the sensor 215 may determine whether the set volume of fluid transferred by the electromagnetic driver comprises an air bubble or liquid, thus permitting the computer processor to calculate the total volume of the liquid transferred from the intermediate container 40 or syringe pump 240 to the destination chamber 44.

In some embodiments, the electromagnetic driver may comprise a stepper motor that transfers a particular volume of fluid in discrete "steps" made by the stepper motor. Each "step" of the stepper motor may correspond to a set volume of fluid being transferred. The computer processor may determine the total volume of fluid transferred corresponding to the number of "steps" the syringe pump 240 is moved. During each "step" of the stepper motor, the sensor 215 may determine whether an air bubble is present in the volume of fluid transferred. If the sensor 215 detects an air bubble during a "step," the computer processor may identify the step as no volume of liquid being transferred to the destination chamber 44. If the sensor 215 does not detect an air bubble during a "step," the computer processor may identify the step as a discrete volume of liquid being transferred to the destination chamber 44. If multiple quantities of liquid have been transferred by multiple "steps," then the computer processor can store in the memory 84 a sum of all the liquid quantities transferred during each "step" identified as liquid being transferred. Upon termination of the fluid transfer sequence, the computer processor may calculate the total sum of all liquid quantities transferred to determine the rate of flow of the fluid transfer and the total volume of liquid transferred.

In some embodiments, the electromagnetic driver may comprise a continuous motor. The computer processor may utilize any one or more structures, components, or steps in the method and systems as described above to calculate the rate of flow and total volume of fluid transferred to the destination chamber 44. The continuous motor may be used in combination with the sensor 215 to measure discrete volume transfers in the continuous motion. The motion of the continuous motor may be identified in discrete "steps" with the motor transferring a set volume of fluid within each "step." The sensor 215 may determine whether the discrete "steps" of fluid transferred by the continuous motor comprise air or liquid. Upon termination of the fluid transfer sequence, the computer processor may calculate the total sum of all liquid quantities transferred to determine the rate of flow of the fluid transfer and the total volume of liquid transferred.

As previously discussed, the sensor 215 may comprise any suitable type of sensor. In some embodiments, the sensor 215 may comprise an acoustic sensor. The acoustic sensor may be used as a sonic device to determine whether a discrete volume of transferred comprises a liquid or air transfer. In some embodiments, the acoustic sensor may comprise a sonic emitter, such as a speaker, and a sonic receiver, such as a microphone. The sonic emitter may produce a sound wave that travels through at least a portion of the fluid transfer module 31 and/or fluid within the fluid transfer module 31 that is being transferred by the electromagnetic driver. The sonic receiver may detect the sound wave after travelling through the fluid, and the sound wave may vary based on whether the wave travelled through a liquid medium or a gaseous medium (e.g., the amplitude, wavelength, pitch, and/or frequency, etc. of the sound wave may vary). The acoustic sensor may use any variations in the received sound wave to determine the presence of air or liquid within an amount of fluid through which the emitted sound wave has passed that is going to be transferred or is being transferred by the electromagnetic driver.

In some embodiments, the acoustic sensor can provide decreased processing requirements, thus increasing response speed, as compared to some other sensor types. The decreased processing requirements and increased response speed can permit the computer processor to increase sampling rates and/or fluid flow rates. The sampling rate may be sufficiently high to provide for generally real-time resolution since the processing requirements of some acoustic sensors are much less than some other types of sensors. The sampling rate can be at least about 30 KHz and/or less than or equal to about 70 KHz. The sensor 125 may comprise an optical sensor. The optical sensor may comprise an optical encoder located in the sensor device 214.

In some embodiments, the electromagnetic driver may be used in combination with sensor 225 to function as a flowmeter similar. While the flowmeter functionality is discussed in terms of transferring fluid from the intermediate container 40 or the syringe pump 240 to the destination container 44 or IV bag 244, it is to be understood that the functionality may apply in any type or combination of fluid transfer devices or otherwise. For example, the electromagnetic driver and the sensor 215 may be used as a flow meter to measure the rate of flow of fluid between the source container 39 or inverted vial 246 and the intermediate container 40 or the syringe pump 240. The application of a flowmeter may apply to fluid transfer from the destination container 44 to the intermediate container 40 or syringe pump 240.

With regard to FIG. 9, if a significant gas bubble is not detected at block 510, then the computer processor can store in a memory 84 the amount of liquid transferred into the intermediate container 40 during block 506. If multiple quantities of fluid have been transferred by multiple iterations of performing block 506, then the computer processor can store in the memory 84 a sum of all of the liquid quantities transferred during each iteration of block 506 performed during this particular liquid transfer process to calculate the total amount of liquid present in the intermediate container 40. The computer processor does not store or add to an amount of transferred in memory during a particular iteration of block 506 if gas is detected at block 510, since the detection of a gas signifies that liquid was not transferred. In some embodiments, such a configuration and/or process can create a flowmeter that determines an amount of liquid transferred over a particular time, by identifying the amount of liquid transferred in each of a plurality of steps, and the time over which such transfers are performed, while not including transfers of fluid that comprise or include air in the flowmeter calculation. As used in this specification, the term "air" can comprise any type of gas (e.g., ambient air or medicinal vapors) and/or an absence of liquid (e.g., a vacuum). If the sum of transferred liquid is approximately equal to an amount specified by the instructions inputted into or transmitted into the fluid transfer management system 74 for the total transfer into the destination container 44, then the withdrawal of liquid from the source container 39 for this particular liquid transfer will end, and the computer processor can proceed to block 516 by sending an electronic signal to the electromechanical driver of the electromechanical controller 36 to actuate the flow-control valve 41 to close the inlet port and open the outlet port to the intermediate container 40 and then the computer processor can send a signal or series of signals to the electromechanical driver to urge the fluid in the intermediate container 40 into the destination container 44. If such sum is less than the amount specified by the instructions inputted into or transmitted into the fluid transfer management system 74 for the total transfer into the destination container 44, then the computer processor can return to block 506 to perform another transfer of a quantity of liquid.

In some embodiments, the memory 84 can store the maximum volume of the particular intermediate container 40 utilized in the fluid transfer module 31. If the sum of fluid transfers during a particular fluid transfer procedure is sufficiently large that another transfer of a quantity of liquid at block 506 will exceed the maximum volume of the intermediate container 40, then the computer processor can actuate the flow-control valve 41 to close off the fluid pathway to the source container 39 and open the fluid pathway between the intermediate container 40 and the destination container 44, and the computer processor can actuate the moveable platform 222 to force the fluid in the intermediate container 40 into the destination container 44. The computer processor can then actuate the flow-control valve 41 to close off the fluid pathway to the destination container 44 and again open the fluid pathway between the source container 39 and the intermediate container 40, and the computer processor can return to block 506 and proceed with the algorithm of FIG. 9 until the specified total amount of fluid has been transferred at block 512.

In some embodiments, the electronic fluid transfer management system 74 can comprise a compliance or verification system with a recorder for capturing and storing information relating to one or more parameters of a particular fluid transfer procedure. For example, in some embodiments, the electronic fluid transfer management system 74 can comprise one or more cameras for capturing one or more images of various components or stages in the transfer of fluid and one or more memories 84 for storing such one or more images. Examples of one or more of such images include an image of the source container 39 (e.g., including the product label on the source container 39), an image of the intermediate container or pumping region 40 when filled with liquid immediately before transferring the liquid into the destination container 44, and/or an image of the destination container 44 when containing or filled with the transferred liquid (e.g., including the patient-information label on the destination container 44). The compliance or verification system can record and store information relating to the patient's identity, the healthcare worker in control of the electronic fluid transfer management system 74 during a particular fluid transfer, the healthcare worker who requested the medical fluid for the patient, the date and time, and/or the type of medical fluid transferred into the destination container, etc. Any or all of this information can be transmitted to and/or retrieved from the patient and/or drug information storage device or network 70.

The fluid transfer module 31 can be manufactured in a series of steps that include providing any or all of the components illustrated and/or described in this specification and/or assembling such components as illustrated and/or described in this specification. In a method of enabling the use of a fluid transfer module 31, a fluid transfer module 31 can be provided to a user and instructions can be provided (e.g., in written form, as part of a display on a screen of a user interface, on a website, in printed directions-for-use, on product packaging, in spoken form, or otherwise) to attach or couple the fluid transfer module 31 to a fluid transfer device 30 that is configured to transfer fluid in any manner disclosed in this specification. For example, any embodiment of a fluid transfer module 31 can be provided to a user, such as the multi-stroke fluid pump assembly 224 of FIG. 2B$_i$ or any of the other fluid modules illustrated and/or described in connection with FIGS. 4, 5, 6, and 6a. Instructions can be provided to the user to attach a fluid transfer module 31 to a fluid transfer device 30 that is configured to perform any of the steps or functions disclosed in this specification, such as steps or procedures involved in priming or purging the fluid transfer module 31 or in pumping fluid between a source container 39 through a fluid transfer module 31 to a destination container 44.

As shown in FIG. 10, in some embodiments, the user interface 78 can be universally compatible with a plurality of different fluid transfer devices 30 and a plurality of different types of fluid transfer devices 30, such as the fluid transfer device 30 of FIG. 2C$_i$, the fluid transfer device 30 of FIG. 2C$_{ii}$, the fluid transfer device 30 of FIG. 4, the fluid transfer device 30 of FIG. 6, and/or the fluid transfer device 30 of FIG. 6a, etc. For example, a single user interface 78 can be configured to electronically communicate with (e.g., by transferring data to and/or from) a plurality of different fluid transfer devices 30 of the same type, or a plurality of different fluid transfer devices 30 of a different type, that are performing separate fluid transfer operations, such as filling destination containers with a plurality of different therapeutic fluids and/or for a plurality of different patients. The user interface 78 can be configured to simultaneously or generally concurrently control and/or record information from any or a plurality or all of such operations. The user interface 78 can comprise a plurality of different communication capabilities, including a plurality of different electronic communicators and/or a plurality of different communication protocols for use with any of such electronic communicators. The user interface 78 can be updated electronically to enable it to communicate electronically using protocols that are not originally used or installed on the user interface, which can enable the user interface 78 to become compatible with future or different types of fluid transfer devices 30, without requiring replacement of the fundamental components of the electronic communication system.

Although this invention has been disclosed in the context of certain embodiments and examples, it will be understood by those skilled in the art that the present invention extends beyond the specifically disclosed embodiments to other alternative embodiments and/or uses of the invention and obvious modifications and equivalents thereof. In addition, while several variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the disclosed invention. Thus, it is intended that the scope of the present invention herein disclosed should not be limited by the particular disclosed embodiments described above, but should be determined only by a fair reading of the claims that follow.

The following is claimed:

1. A medical fluid transfer module that is configured to be removably coupled to an electronic medical fluid transfer device to facilitate the transfer of medical fluids from a source container to a destination container, the electronic medical fluid transfer device comprising a first electromechanical driver, a second electromechanical driver, and an attachment portion configured to couple with the medical fluid transfer module, the medical fluid transfer module comprising:

a first closeable, resealable medical connector and a second closeable, resealable medical connector;

a multidirectional flow-control valve with a rotatable driving interface configured to interface with a first electromechanical driver of an electronic medical fluid transfer device, the multidirectional flow-control valve comprising a plurality of functional positions to enable a selection among a plurality of different fluid pathways within the medical fluid transfer module, the rotatable driving interface being further configured to rotate to selectively transition between the plurality of different fluid pathways; and an intermediate container configured to be coupled with an attachment portion of the electronic medical fluid transfer device and configured to interface with a second electromechanical driver of the electronic medical fluid transfer device, wherein the rotatable driving interface is further configured to be rotatable relative to the intermediate container such that the intermediate container may remain stationary and remain interfaced with the second electromechanical driver of the electronic medical fluid transfer device while the rotatable driving interface selectively transitions between the plurality of different fluid pathways, and wherein the plurality of different fluid pathways are configured to contain liquid within the medical fluid transfer module in a closed system when the medical fluid transfer module is not attached to the electronic medical fluid transfer device.

2. The combination of the medical fluid transfer module of claim 1 and the electronic medical fluid transfer device.

3. The medical fluid transfer module of claim 1, wherein the rotatable driving interface comprises a shape that is configured to be complementary with or generally match or correspond with a driving interface of the electromechanical driver of the electronic medical fluid transfer device.

4. The medical fluid transfer module of claim 1 further comprising a valve handle configured to be manipulated to actuate the multidirectional flow-control valve to selectively transition between the plurality of different fluid pathways.

5. The medical fluid transfer module of claim 1, wherein the rotatable driving interface is removably engaged with the electronic medical fluid transfer device.

6. A method of enabling medical fluid transfer between a source container and a destination container, the method comprising the steps of:

providing a closed-system fluid transfer module comprising:
　　a first closeable, resealable medical connector and a second closeable, resealable medical connector,
　　a multidirectional fluid control valve with a rotatable driving interface configured to interface with a first electromechanical driver of an electronic medical fluid transfer device, and
　　an intermediate container or an intermediate pumping region configured to be coupled with an attachment portion of the electronic medical fluid transfer device and configured to interface with a second electromechanical driver of the electronic medical fluid transfer device,
　　wherein the rotatable driving interface is further configured to be rotatable relative to the intermediate container or the intermediate pumping region such that the intermediate container or the intermediate pumping region may remain interfaced with a second electromechanical driver of the electronic medical fluid transfer device while the rotatable driving interface selectively transitions between the plurality of different fluid pathways; and
wherein the closed-system fluid transfer module is configured to couple with the electronic medical fluid transfer device.

7. The method of claim 6 further comprising the step of providing the electronic medical fluid transfer device.

8. The method of claim 6, wherein the rotatable driving interface is removably engaged with the electronic medical fluid transfer device.

* * * * *